US 11,559,516 B2

(12) United States Patent
Mehrling et al.

(10) Patent No.: US 11,559,516 B2
(45) Date of Patent: *Jan. 24, 2023

(54) PHARMACEUTICAL COMBINATIONS FOR TREATING CANCER

(71) Applicant: Purdue Pharmaceutical Products L.P., Stamford, CT (US)

(72) Inventors: Thomas Jorg Mehrling, Basel (CH); Enrique Maria Ocio, Salamanca (ES)

(73) Assignee: Purdue Pharmaceutical Products L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/212,765

(22) Filed: Mar. 25, 2021

(65) Prior Publication Data
US 2021/0346351 A1 Nov. 11, 2021

Related U.S. Application Data

(63) Continuation of application No. 16/517,936, filed on Jul. 22, 2019, now abandoned, which is a continuation of application No. 15/985,097, filed on May 21, 2018, now Pat. No. 10,406,138, which is a continuation of application No. 15/314,162, filed as application No. PCT/EP2015/061571 on May 26, 2015, now abandoned.

(30) Foreign Application Priority Data

May 28, 2014 (GB) ...................... 1409471

(51) Int. Cl.
*A61K 31/4184* (2006.01)
*A61K 38/06* (2006.01)
*A61K 31/407* (2006.01)
*A61K 31/427* (2006.01)
*A61K 31/5377* (2006.01)
*A61K 31/573* (2006.01)
*A61K 31/58* (2006.01)
*A61K 31/69* (2006.01)
*A61K 38/05* (2006.01)
*A61K 31/502* (2006.01)
*A61K 31/55* (2006.01)
*A61K 39/395* (2006.01)
*A61K 45/06* (2006.01)

(52) U.S. Cl.
CPC ........ *A61K 31/4184* (2013.01); *A61K 31/407* (2013.01); *A61K 31/427* (2013.01); *A61K 31/502* (2013.01); *A61K 31/5377* (2013.01); *A61K 31/55* (2013.01); *A61K 31/573* (2013.01); *A61K 31/58* (2013.01); *A61K 31/69* (2013.01); *A61K 38/05* (2013.01); *A61K 38/06* (2013.01); *A61K 39/3955* (2013.01); *A61K 45/06* (2013.01)

(58) Field of Classification Search
CPC .............. A61K 31/4184; A61K 31/407; A61K 31/427; A61K 31/502; A61K 31/5377; A61K 31/55; A61K 31/573; A61K 31/58; A61K 31/69; A61K 38/05; A61K 38/06; A61K 39/3955; A61K 45/06
USPC ....................................... 514/19.4
See application file for complete search history.

(56) References Cited

U.S. PATENT DOCUMENTS

| 4,522,811 | A | 6/1985 | Eppstein et al. |
| 5,134,127 | A | 7/1992 | Stella et al. |
| 5,376,645 | A | 12/1994 | Stella et al. |
| 5,571,534 | A | 11/1996 | Jalonen et al. |

(Continued)

FOREIGN PATENT DOCUMENTS

| CL | 0501-2003 | 3/2003 |
| CL | 2272-2005 | 9/2005 |

(Continued)

OTHER PUBLICATIONS

Advanced Accelerator Applications, Ongoing Clinical Studies with Advanced Accelerator Applications Pipeline Candidates. Retrieved online at: http://www.adacap.com/research-development/clinical-trials/. 6 pages, (2014).

(Continued)

*Primary Examiner* — Kristin A Vajda
(74) *Attorney, Agent, or Firm* — McCarter & English, LLP; Yu Lu

(57) ABSTRACT

The present invention is directed to a combination comprising a proteasome inhibitor and a compound of formula I or a pharmaceutically acceptable salt thereof:

to a pharmaceutical composition and to a kit both comprising said combination, to the combination, composition or kit for use in the treatment of cancer, and to a method of treatment of cancer in a patient in need thereof comprising administering to said patient an effective amount of said combination, composition or kit.

9 Claims, 15 Drawing Sheets

(56) References Cited

U.S. PATENT DOCUMENTS

| | | |
|---|---|---|
| 5,874,418 A | 2/1999 | Stella et al. |
| 6,046,177 A | 4/2000 | Stella et al. |
| 6,087,367 A | 7/2000 | Breslow et al. |
| 6,133,248 A | 10/2000 | Stella |
| 6,214,852 B1 | 4/2001 | Kim et al. |
| 6,407,079 B1 | 6/2002 | Muller et al. |
| 8,461,350 B2 | 6/2013 | Brittain et al. |
| 8,609,864 B2 | 12/2013 | Chen et al. |
| 8,962,855 B2 | 2/2015 | Chen et al. |
| 9,096,627 B2 | 8/2015 | Chen et al. |
| 9,376,395 B2 | 6/2016 | Chen et al. |
| RE46,144 E | 9/2016 | Chen et al. |
| 9,889,147 B2 | 2/2018 | Utku |
| 9,993,482 B2 | 6/2018 | Mehrling |
| 10,118,901 B2 | 11/2018 | Chen et al. |
| 10,406,138 B2 | 9/2019 | Mehrling et al. |
| 10,744,120 B2 | 8/2020 | Mehrling et al. |
| 11,318,117 B2 | 5/2022 | Mehrling et al. |
| 2002/0076409 A1 | 6/2002 | March et al. |
| 2006/0079528 A1 | 4/2006 | Finn et al. |
| 2006/0159713 A1 | 7/2006 | Brittain et al. |
| 2008/0146556 A1 | 6/2008 | Diebold et al. |
| 2010/0022512 A1 | 1/2010 | Wisdom et al. |
| 2010/0216858 A1 | 8/2010 | Popek et al. |
| 2011/0190363 A1 | 8/2011 | Drager et al. |
| 2011/0269706 A1 | 11/2011 | Chen et al. |
| 2011/0311624 A1 | 12/2011 | Loury et al. |
| 2012/0289570 A1 | 11/2012 | Lengyel et al. |
| 2013/0030237 A1 | 1/2013 | Theuer |
| 2013/0209558 A1 | 8/2013 | Patzak et al. |
| 2014/0303218 A1 | 10/2014 | Chen et al. |
| 2015/0086551 A1 | 3/2015 | Chen et al. |
| 2015/0231198 A1 | 8/2015 | Carniti et al. |
| 2017/0095482 A1 | 4/2017 | Mehrling |
| 2017/0151218 A1 | 6/2017 | Mehrling et al. |
| 2017/0296513 A1 | 10/2017 | Mehrling et al. |
| 2018/0098969 A1 | 4/2018 | Mehrling et al. |
| 2019/0343807 A1 | 11/2019 | Mehrling et al. |
| 2020/0113870 A1 | 4/2020 | Mehrling |
| 2020/0230109 A1 | 7/2020 | Mehrling |
| 2020/0261423 A1 | 8/2020 | Mehrling |
| 2020/0397759 A1 | 12/2020 | Mehrling et al. |
| 2021/0059989 A1 | 3/2021 | Mehrling et al. |
| 2022/0016084 A1 | 1/2022 | Hilgier et al. |
| 2022/0016085 A1 | 1/2022 | Hilgier et al. |

FOREIGN PATENT DOCUMENTS

| | | |
|---|---|---|
| CL | 3232-2006 | 11/2006 |
| CN | 1764648 A | 4/2006 |
| CN | 101084876 A | 12/2007 |
| CN | 101928234 A | 12/2010 |
| CN | 102993102 A | 3/2013 |
| DE | 34727 A1 | 12/1964 |
| EP | 0717638 B1 | 3/2002 |
| EP | 3148529 A1 | 4/2017 |
| JP | 2007-531793 A | 11/2007 |
| KR | 10-2001-0031896 A | 4/2001 |
| WO | WO-1995/030442 A1 | 11/1995 |
| WO | WO-2002/010161 A1 | 2/2002 |
| WO | WO-2002/22577 A2 | 3/2002 |
| WO | WO-2002/026696 A1 | 4/2002 |
| WO | WO-2002/055017 A2 | 7/2002 |
| WO | WO-2004/076386 A2 | 9/2004 |
| WO | WO-2005/013958 A1 | 2/2005 |
| WO | WO-2005/097747 A1 | 10/2005 |
| WO | WO-2006/120456 A1 | 11/2006 |
| WO | WO-2007/134169 A2 | 11/2007 |
| WO | WO-2008/050125 A1 | 5/2008 |
| WO | WO-2008/067027 A2 | 6/2008 |
| WO | WO-2009/036016 A1 | 3/2009 |
| WO | WO-2009/067453 A1 | 5/2009 |
| WO | WO-2009/100045 A1 | 8/2009 |
| WO | WO-2010/042568 A1 | 4/2010 |
| WO | WO-2010/075542 A1 | 7/2010 |
| WO | WO-2010/085377 A2 | 7/2010 |
| WO | WO-2010/097700 A1 | 9/2010 |
| WO | WO-2011/017448 A1 | 2/2011 |
| WO | WO-2013/039488 A1 | 3/2013 |
| WO | WO-2013/040286 A2 | 3/2013 |
| WO | WO-2013/113838 A1 | 8/2013 |
| WO | WO-2015/085289 A1 | 6/2015 |
| WO | 2015/180865 A1 | 12/2015 |
| WO | 2015/181156 A1 | 12/2015 |
| WO | WO-2015/181154 A1 | 12/2015 |
| WO | WO-2015/181157 A1 | 12/2015 |
| WO | WO-2016/087950 A1 | 6/2016 |
| WO | 2017/067474 A1 | 4/2017 |

OTHER PUBLICATIONS

Aguado Bueno et al., Preliminary Experience of the Spanish Compassionate Use Registry of Bendamustine in Patients with Relapsed and/or Refractory Multiple Myeloma. Blood. 2012;120(21), Abstract 4035.

Al-Ani et al., Changes in urinary metabolomic profile during relapsing renal vasculitis. Sci Rep. Dec. 1, 2016;6:38074. 11 pages.

Alfarouk et al., Resistance to cancer chemotherapy: failure in drug response from ADME to P-gp. Cancer Cell Int. Jul. 15, 2015;15:71.

American Cancer Society, How does chemotherapy affect the risk of second cancers? Retrieved online at: https://www.cancer.org/treatment/treatments-and-side-effects/physical-side-effects/second-cancers-in-adults/chemotherapy.html. 5 pages (2017).

Anastasia et al., Bendamustine for Hodgkin lymphoma patients failing autologous or autologous and allogeneic stem cell transplantation: a retrospective study of the Fondazione Italiana Linfomi. Br J Haematol. Jul. 2014;166(1):140-2.

Andersson et al., Discovery of novel drug sensitivities in T-PLL by high-throughput ex vivo drug testing and mutation profiling. Leukemia. Aug. 14, 2017. pp. 1-14.

Andersson et al., Primary T-Prolymphocytic Leukemia (T-PLL) Cells Are Sensitive To BCL-2 and HDAC Inhibitors: Results From High-Throughput Ex Vivo Drug Testing. Blood. 2013;122:3828. 6 pages.

Angelucci et al., Suberoylanilide hydroxamic acid partly reverses resistance to paclitaxel in human ovarian cancer cell lines. Gynecol Oncol. Dec. 2010;119(3):557-63.

Arun et al., The PARP inhibitor AZD2281 (Olaparib) induces autophagy/mitophagy in BRCA1 and BRCA2 mutant breast cancer cells. Int J Oncol. Jul. 2015;47(1):262-8.

Attal et al., Lenalidomide, Bortezomib, and Dexamethasone with Transplantation for Myeloma. The New England Journal of Medicine. Apr. 6, 2017;376:1311-1320.

Audeh et al., Oral poly(ADP-ribose) polymerase inhibitor olaparib in patients with BRCA1 or BRCA2 mutations and recurrent ovarian cancer: a proof-of-concept trial. Lancet. Jul. 24, 2010;376(9737):245-51.

Bachmann et al., Epigenetic silencing of BIM in glucocorticoid poor-responsive pediatric acute lymphoblastic leukemia, and its reversal by histone deacetylase inhibition. Blood. Oct. 21, 2010;116(16):3013-22.

Bagchi, Bendamustine for advanced sarcoma. Lancet Oncol. Aug. 2007;8(8):674.

Balfour et al., Bendamustine. Drugs. 2001;61(5):631-8.

Barendsen et al., Inhibition of TPA-induced monocytic differentiation in THP-1 human monocytic leukemic cells by staurosporine, a potent protein kinase C inhibitor. Leuk Res. 1990;14(5):467-74.

Berenson et al., Phase I/II trial assessing bendamustine plus bortezomib combination therapy for the treatment of patients with relapsed or refractory multiple myeloma. Br J Haematol. Feb. 2013;160(3):321-30.

Bernhard et al., Quality of life and quality-adjusted survival (Q-TWiST) in patients receiving dose-intensive or standard dose chemotherapy for high-risk primary breast cancer. Br J Cancer. Jan. 15, 2008;98(1):25-33.

Besse et al., The first in class, alkylator-histone-deacetylase-inhibitor fusion molecule EDO-S101 in combination with protea-

(56) References Cited

OTHER PUBLICATIONS some inhibitors induces highly synergistic pro-apoptotic signaling through UPR activation and suppression of c-Myc and BCL2 in multiple meyloma. ASH, 2016.

Besse et al., The first-in-class alkylating HDAC inhibitor EDO-S101 is highly synergistic with proteasome inhibition against multiple myeloma through activation of multiple pathways. Blood Cancer J. Jul. 2017;7(7):e589. 4 pages.

Besse et al., The First-in-Class, Alkylator-Histone-Deacetylase-Inhibitor Fusion Molecule EDO-S101 in Combination with Proteasome Inhibitors Induces Highly Synergistic Pro-Apoptotic Signaling through UPR Activation and Suppression of c-MYC and BCL2 in Multiple Myeloma. 58th ASH Annual Meeting, San Diego, Dec. 3-6, 2016, Publication No. 4466. 1 page.

Biete et al., Whole abdominal radiotherapy in ovarian cancer. Rep Pract Oncol Radiother. Mar. 23, 2010;15(2):27-30.

Blattmann et al., Enhancement of radiation response in osteosarcoma and rhabdomyosarcoma cell lines by histone deacetylase inhibition. Int J Radiat Oncol Biol Phys. Sep. 1, 2010;78(1):237-45.

Bose et al., Histone deacetylase inhibitor (HDACI) mechanisms of action: emerging insights. Pharmacol Ther. Sep. 2014;143(3):323-36.

Botrugno et al., Molecular pathways: old drugs define new pathways: non-histone acetylation at the crossroads of the DNA damage response and autophagy. Clin Cancer Res. May 1, 2012;18(9):2436-42.

Braga et al., Crystal Polymorphism and Multiple Crystal Forms. Struct Bond. 2009;132:25-50.

Brewster et al., Cyclodextrins as pharmaceutical solubilizers. Adv Drug Deliv Rev. Jul. 30, 2007;59(7):645-66.

Bruce et al., Glioblastoma Multiforme Treatment & Management. Medscape. Retrieved online at: https://emedicine.medscape.com/article/283252-treatment. 20 pages. Jun. 14, 2017.

Buglio et al., Histone deacetylase inhibitors in Hodgkin lymphoma. Invest New Drugs. Dec. 2010;28 Suppl 1:S21-7.

Buglio et al., Vorinostat inhibits STAT6-mediated TH2 cytokine and TARC production and induces cell death in Hodgkin lymphoma cell lines. Blood. Aug. 15, 2008;112(4):1424-33.

Cai et al., Combination of bendamustine and entinostat synergistically inhibits proliferation of multiple myeloma cells via induction of apoptosis and DNA damage response. Cancer Lett. Jul. 28, 2013;335(2):343-50.

Cai et al., Discovery of 7-(4-(3-ethynylphenylamino)-7-methoxyquinazolin-6-yloxy)-N-hydroxyheptanamide (CUDc-101) as a potent multi-acting HDAC, EGFR, and HER2 inhibitor for the treatment of cancer. J Med Chem. Mar. 11, 2010;53(5):2000-9.

Cai et al., Solubilization of vorinostat by cyclodextrins. J Clin Pharm Ther. Oct. 2010;35(5):521-6.

Campos et al., Expression of nuclear receptor corepressors and class I histone deacetylases in astrocytic gliomas. Cancer Sci. Feb. 2011;102(2):387-92.

Chamberlain et al., Salvage therapy with bendamustine for methotrexate refractory recurrent primary CNS lymphoma: a retrospective case series. J Neurooncol. May 2014;118(1):155-62.

Chamberlain et al., Salvage therapy with single agent bendamustine for recurrent glioblastoma. J Neurooncol. Dec. 2011;105(3):523-30.

Chen et al., A 71-gene signature of TRAIL sensitivity in cancer cells. Mol Cancer Ther. Jan. 2012;11(1):34-44.

Chen et al., Discovery of a Novel, Efficient, and Scalable Route to Bendamustine Hydrochloride: The API in Treanda. Org Process Res Dev. 2011;15(5):1063-1072.

Chesi et al., Drug response in a genetically engineered mouse model of multiple myeloma is predictive of clinical efficacy. Blood. Jul. 12, 2012;120(2):376-85.

Chesi et al., Identification of Novel Therapeutic Targets in the Clinically Predictive Vk*MYC Mouse Model of Multple Myeloma. ASH, 2 pages. 2014.

Chesi et al., Identification of Novel Therapeutic Targets in the Clinically Predictive Vk*MYC Mouse Model of Multple Myeloma. Blood. 2014;124:415.

Chisholm et al., Emergence of drug tolerance in cancer cell populations: an evolutionary outcome of selection, nongenetic instability, and stress-induced adaptation. Cancer Res. Mar. 15, 2015;75(6):930-9.

Chiu et al., Suberoylanilide hydroxamic acid, an inhibitor of histone deacetylase, enhances radiosensitivity and suppresses lung metastasis in breast cancer in vitro and in vivo. PLoS One. Oct. 10, 2013;8(10):e76340. 12 pages.

Choi et al., Enhanced cytotoxic effect of radiation and temozolomide in malignant glioma cells: targeting PI3K-AKT-mTOR signaling, HSP90 and histone deacetylases. BMC Cancer. Jan. 13, 2014;14:17. 12 pages.

Chow et al., In vitro induction of apoptosis of neoplastic cells in low-grade non-Hodgkin's lymphomas using combinations of established cytotoxic drugs with bendamustine. Haematologica. May 2001;86(5):485-93.

Ciavatta et al., Epigenetic basis for aberrant upregulation of autoantigen genes in humans with ANCA vasculitis. J Clin Invest. Sep. 2010;120(9):3209-19.

Ciusani et al., Valproic acid increases the in vitro effects of nitrosureas on human glioma cell lines. Oncol Res. 2007;16(10):453-63.

ClinicalTrials.gov, A Phase 1 Study to Investigate the Safety, Pharmacokinetic Profiles and the Efficacy of EDO-S101, a First-in-Class Alkylating Histone Deacetylase Inhibition (HDACi) Fusion Molecule, in Relapsed/Refractory Hematologic Malignancies. Clinical Trials Identifier: NCT02576496, Oct. 14, 2015. 5 pages.

ClinicalTrials.gov, Bendamustine, Lenalidomide (Revlimid®) and Dexamethasone (BRd) as 2nd-line Therapy for Patients With Relapsed or Refractory Multiple Myeloma (BRd). Clinical Trials Identifier: NCT01701076, Aug. 24, 2016.

ClinicalTrials.gov, Phase 1 Trial of Dasatinib and Bendamustine in Chronic Lymphocytic Leukemia. ClinicalTrials Identifier: NCT00872976, Apr. 22, 2009. 3 pages.

Connors, Hodgkin lymphoma: special challenges and solutions. Hematol Oncol. Jun. 2015;33 Suppl 1:21-4.

Cooke et al., Spontaneous onset and transplant models of the Vk*MYC mouse show immunological sequelae comparable to human multiple myeloma. J Transl Med. Sep. 6, 2016;14:259. 12 pages.

Corazzelli et al., Efficacy and safety of bendamustine for the treatment of patients with recurring Hodgkin lymphoma. Br J Haematol. Jan. 2013;160(2):207-15.

Curigliano et al., Cardiovascular toxicity induced by chemotherapy, targeted agents and radiotherapy: ESMO Clinical Practice Guidelines. Annals of Oncology. Oct. 2012;23(Suppl. 7):vii155-vii166.

De Filippi et al., "The First-in-Class Alkylating Histone-Deacetylase Inhibitor(HDACi) Fusion Molecule Edo-S101 Exerts Potent Preclinical Activity Against Tumor Cells of Hodgkin Lymphoma (HL) Including Bendamustine-Resistant Clones" ASH, 57th annual meeting and exposition, Dec. 2015, Abstract 2481.

De Filippi et al., Continuous Exposure to Bendamustine (BPM) Results in Stable Upregulation of CD30 and Increased Sensitivity to Brentuximab Vedotin (BV) in Tumor Cells of Hodgkin Lymphoma HL. Istituto Nazionale Tumor, IRCCS-Fondazione Pascale, Dec. 6, 2015. 1k page.

De Filippi et al., Edo-S101, a Bendamustine (BDM)/Histone-Deacetylase Inhibitor (HDACi) Fusion Molecule, Demonstrates Potent Preclinical Activity Against T-Cell Malignancies and Overcomes BDM-Resistance. ASH, 59th Annual Meeting & Exposition. Dec. 9-12, 2017. Poster 2547. 1 page.

De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. ASH 57th Annual Meeting & Exposition. Abstract No. 2481. Dec. 5-8, 2015 [Downloaded from: [https://ash.confex.com/ash/2015/webprogram/Paper84797.html]. 2 pages.

Deangelo et al., Phase 1 clinical results with tandutinib (MLN518), a novel FLT3 antagonist, in patients with acute myelogenous leukemia or high-risk myelodysplastic syndrome: safety, pharmacokinetics, and pharmacodynamics. Blood. Dec. 1, 2006;108(12):3674-81.

(56) References Cited

OTHER PUBLICATIONS

Desouza et al., Has the survival of patients with glioblastoma changed over the years? Br J Cancer. Jan. 19, 2016;114(2):146-50.
Diehl, The Evolution of Chemotherapy, Using the A-DAC Principle to Unlock New Treatment Options in Hodgkin Lymphoma. Mundipharma EDO Satellite Symposium, 10th International Symposium on Hodgkin Lymphoma, 6 pages, Oct. 23, 2016.
Dooley et al., Alkylating Histone Deacetylase Inhibitor Treatment in Animal Models of MPO-ANCA Vasculitis. Abstract TH-PO052. Asn, Kidney Week, Nov. 2, 2017, 2 pages.
Drogaris et al., Histone deacetylase inhibitors globally enhance h3/h4 tail acetylation without affecting h3 lysine 56 acetylation. Sci Rep. 2012;2:220. 12 pages.
Döhner et al., Diagnosis and management of acute myeloid leukemia in adults: recommendations from an international expert panel, on behalf of the European LeukemiaNet. Blood. Jan. 21, 2010;115(3):453-74.
edoncology.com, The A-DAC Principle: A New Concept in Oncology Treatment. 3 pages, Sep. 2016.
EU Clinical Trials Register, EudraCT No. 2005-002051-41. 13 pages. Dec. 7, 2016.
EU Clinical Trials Register, EudraCT No. 2005-006083-57. 28 pages. Jun. 1, 2016.
Eurordis, Rare Diseases Europe, Why Research on Rare Diseases? Position Paper. Retrieved online at: www.eurordis.org. 14 pages. Oct. 2010.
Fei et al., Development of clinically relevant orthotopic xenograft mouse model of metastatic lung cancer and glioblastoma through surgical tumor tissues injection with trocar. J Exp Clin Cancer Res. Jun. 29, 2010;29:84.
Festuccia et al., Enhancement of radiosensitivity by the novel anticancer quinolone derivative vosaroxin in preclinical glioblastoma models. EJC, European Journal of Cancer. Dec. 2016;69(Suppl 1):S62. Abstract 174, Poster P145.
Festuccia et al., Targeting glioblastoma with UniPR1331, a new and stable bioavailable small molecule inhibiting Ephephrin interaction: In vitro and in vivo evidence. EJC, European Journal of Cancer. Dec. 2016;69(Suppl 1), Abstract 71, Poster P042.
Festuccia et al., The first-in-class alkylating deacetylase inhibitor molecule tinostamustine shows antitumor effects and is synergistic with radiotherapy in preclinical models of glioblastoma. J Hematol Oncol. Feb. 27, 2018;11(1):32. 19 pages.
Frew et al., Enhancing the apoptotic and therapeutic effects of HDAC inhibitors. Cancer Lett. Aug. 8, 2009;280(2):125-33.
Furumai et al., Potent histone deacetylase inhibitors built from trichostatin A and cyclic tetrapeptide antibiotics including trapoxin. Proc Natl Acad Sci U S A. Jan. 2, 2001;98(1):87-92.
Geurink et al., Incorporation of non-natural amino acids improves cell permeability and potency of specific inhibitors of proteasome trypsin-like sites. J Med Chem. Feb. 14, 2013;56(3):1262-75.
Ghesquières et al., Clinical experience of bendamustine in relapsed or refractory Hodgkin lymphoma: a retrospective analysis of the French compassionate use program in 28 patients. Leuk Lymphoma. Nov. 2013;54(11):2399-404.
Gillis, HDAC Inhibition Appears to Sensitive Triple-Negative Breast Cancer Cells to Certain Treatments. Retrieved online at: https://www.onclive.com/conference-coverage/sabcs-2012/hdac-inhibition-appears-to-sensitize-triplenegative-breast-cancer-cells-to-certain-treatment, 2 pages, (2012).
Golub et al., Molecular classification of cancer: class discovery and class prediction by gene expression monitoring. Science. Oct. 15, 1999;286(5439):531-7.
Graham et al., T-cell prolymphocytic leukemia. Proc (Bayl Univ Med Cent). Jan. 2013;26(1):19-21.
Greaves et al., Clonal evolution in cancer. Nature. Jan. 18, 2012;481(7381):306-13.
Griffith et al., A novel anti-cancer bifunctional platinum drug candidate with dual DNA binding and histone deacetylase inhibitory activity. Chem Commu (Camb). Nov. 28, 2009;(44):6735-7.

Griffith et al., Novel Platinum Pyridinehydroxamic Acid Complexes: Synthesis, Characterisation, X-ray Crystallographic Study of Nitric Oxide Related Properties. Polyhedron. 2007;26:4697-4706.
Groselj et al., Histone deacetylase inhibitors as radiosensitisers: effects on DNA damage signalling and repair. Br J Cancer. Mar. 5, 2013;108(4):748-54.
Hancock et al., HDAC inhibitor therapy in autoimmunity and transplantation. Ann Rheum Dis. Apr. 2012;71 Suppl 2:i46-54.
Harrison et al., High Response Rates with the Combination of Bortezomib. Dexamethasone and the Pan-HistoneDeacetylase Inhibitor Romidepsin in Patients with Relapsed or Refractory Multiple Myeloma in a Phase 1/11 Clinical Trial. Blood. 2008;112, Abstract 3698. ASH Annual Meeting.
Hedgethorne et al., Foretinib, c-Met and VEGFR-2 Inhibitor Oncolytic. Drugs of the Future. 2010;35(11):893-902.
Hegi et al., MGMT gene silencing and benefit from temozolomide in glioblastoma. N Engl J Med. Mar. 10, 2005;352(10):997-1003.
Her et al., Targeting DNA Double-strand Break Repair in Cancer Therapy. Journal of Molecular and Genetic Medicine. Dec. 31, 2015;9:e106, 1 page.
Herold et al., Bendamustine, vincristine and prednisone (BOP) versus cyclophosphamide, vincristine and prednisone (COP) in advanced indolent non-Hodgkin's lymphoma and mantle cell lymphoma: results of a randomised phase III trial (OSHO# 19). J Cancer Res Clin Oncol. Feb. 2006;132(2):105-12.
Herold et al., BOP versus COP in Advanced Low Grade Non-Hodgkin's Lymphomas—Results of a Randomized Multicenter Study. Blood. 1999;94:262b. Abstract 4382.
Hideshima et al., Mechanism of action of proteasome inhibitors and deacetylase inhibitors and the biological basis of synergy in multiple myeloma. Mol Cancer Ther. Nov. 2011;10(11):2034-42.
Hoffman, Brentuximab Vedotin Plus Bendamustine Active In Heavily Pretreated Hodgkin Lymphoma, ALCL. Cancer Therapy Advisor, Dec. 7, 2015. 2 pages, retreived online at: http://www.cancertherapyadvisor.com/ash-2015/hodgkin-lymphoma-alcl-brentuximab-vedotin-better-treatment-risk/article/458249/.
Hong et al., Complete Durable Response From Carboplatin and Olaparib in a Heavily Pretreated Triple-Negative Metastatic Breast Cancer With Germline BRCA2 and "BRCAness" Mutations. J Oncol Pract. Mar. 2016;12(3):270-2.
Howlader et al., Contributions of Subtypes of Non-Hodgkin Lymphoma to Mortality Trends. Cancer Epidemiol Biomarkers Prev. Jan. 2016;25(1):174-9.
Ihle et al., HR23b expression is a potential predictive biomarker for HDAC inhibitor treatment in mesenchymal tumours and is associated with response to vorinostat. The Journal of Pathology: Clinical Research. 2016;2:59-71.
Jagannath et al., Bortezomib in combination with dexamethasone for the treatment of patients with relapsed and/or refractory multiple myeloma with less than optimal response to bortezomib alone. Haematologica. Jul. 2006;91(7):929-34.
Jawhari et al., In Vitro and In Vivo Preclinical Activity of EDO-S101 in Hodgkin Lymphoma. Haematologica. 2016;101(s5):6-7, Abstract P037.
Jennette et al., Pathogenesis of antineutrophil cytoplasmic autoantibody-mediated disease. Nat Rev Rheumatol. Aug. 2014;10(8):463-73.
Jiang et al., A mammalian functional-genetic approach to characterizing cancer therapeutics. Nature Chemical Biology. Feb. 2011;7:92-100.
Kaddour et al., Transmission of Induced Chromosomal Aberrations through Successive Mitotic Divisions in Human Lymphocytes after In Vitro and ?In? Vivo Radiation. Scientific Reports. Jun. 12, 2017;7:3291, 11 pages.
Kalin et al., Creating zinc monkey wrenches in the treatment of epigenetic disorders. Curr Opin Chem Biol. Jun. 2009;13(3):263-71.
Kallenberg, Pathogenesis and treatment of ANCA-associated vasculitides. Clin Exp Rheumatol. Jul.-Aug. 2015;33(4 Suppl 92):S11-4.
Kallenberg, Pathogenesis of ANCA-associated vasculitides. Ann Rheum Dis. Mar. 2011;70 Suppl 1:i59-63.

(56) References Cited

OTHER PUBLICATIONS

Kalsi et al., The impact of low-grade toxicity in older people with cancer undergoing chemotherapy. Br J Cancer. Dec. 9, 2014;111(12):2224-8.
Kampa-Schittenhelm et al., Quizartinib (AC220) is a potent second generation class III tyrosine kinase inhibitor that displays a distinct inhibition profile against mutant-FLT3, -PDGFRA and -KIT isoforms. Molecular Cancer. 2013;12:19, 15 pages.
Kaufman et al., Lenalidomide. Bortezomib. and Dexamethasone (RVD) in Combination with Vorinostat As Front-Line Therapy for Patients with Multiple Myeloma (MM): Results of a Phase 1 Study. Blood. 2012;120, Abstract No. 336. 2 pages. ASH Annual Meeting.
Keating et al., Bendamustine. Nat Rev Drug Discov. Jun. 2008;7(6):473-4.
Khot et al., Panobinostat in lymphoid and myeloid malignancies. Expert Opin Investig Drugs. Sep. 2013;22(9):1211-23.
Kigawa, New strategy for overcoming resistance to chemotherapy of ovarian cancer. Yonago Acta Med. Jun. 2013;56(2):43-50.
Kim et al., Histone deacetylase inhibitors: molecular mechanisms of action and clinical trials as anti-cancer drugs. Am J Transl Res. Feb. 2011;3(2):166-79.
Knauf, Bendamustine in the treatment of chronic lymphocytic leukemia. Expert Rev Anticancer Ther. Feb. 2009;9(2):165-74.
Knittel et al., Two mouse models reveal an actionable PARP1 dependence in aggressive chronic lymphocytic leukemia. Nat Commun. Jul. 28, 2017;8(1):153. 13 pages.
Kollmannsberger et al., Phase II study of bendamustine in patients with relapsed or cisplatin-refractory germ cell cancer. Anticancer Drugs. Aug. 2000;11(7):535-9.
Kotzin et al., Reversal of nzb/nzw disease with total lymphoid irradiation. J Exp Med. Aug. 1, 1979;150(2):371-8.
Kraus et al., EDO-S101, A New Alkylating Histone-Deacetylase Inhibitor (HDAC) Fusion Molecule has Superior Activity Against Myeloma and B Cell Lympoma and Strong Synergy, With Proteasome Inhibitors in vitro. ASH, 2014.
Kraus et al., EDO-S101, A New Alkylating Histone-Deacetylase Inhibitor (HDACi) Fusion Molecule, has Superior Activity Against Myeloma and B Cell Lympoma and Strong Synergy With Proteasome Inhibitors in vitro. ASH, 2014. Publication No. 2249.
Kraus et al., EDO-S101, A New Alkylating Histone-Deacetylase Inhibitor (HDACi) Fusion Molecule, Has Superior Activity Against Myeloma and B Cell Lympoma and Strong Synergy with Proteasome Inhibitors in vitro. Blood. 2014;124;2249.
Krause et al., Tyrosine kinases as targets for cancer therapy. N Engl J Med. Jul. 14, 2005;353(2):172-87.
Kumar et al., Histone deacetylase inhibitors induce cell death in supratentorial primitive neuroectodermal tumor cells. Oncol Rep. Nov. 2006;16(5):1047-52.
Lala et al., Role of nitric oxide in tumor progression: lessons from experimental tumors. Cancer Metastasis Rev. Mar. 1998;17(1):91-106.
Layman et al., Severe and prolonged lymphopenia observed in patients treated with bendamustine and erlotinib for metastatic triple negative breast cancer. Cancer Chemother Pharmacol. May 2013;71(5):1183-90.
Le Moigne et al., The p97 Inhibitor CB-5083 Is a Unique Disrupter of Protein Homeostasis in Models of Multiple Myeloma. Molecular Cancer Therapeutics. Nov. 2017;16(11):2375-2386.
Lee et al., Phase I/Ib study of olaparib and carboplatin in BRCA1 or BRCA2 mutation-associated breast or ovarian cancer with biomarker analyses. J Natl Cancer Inst. May 19, 2014;106(6):dju089. 11 pages.
Lehmann et al., Refinement of Triple-Negative Breast Cancer Molecular Subtypes: Implications for Neoadjuvant Chemotherapy Selection. PLoS One. Jun. 16, 2016;11(6):e0157368, 22 pages.
Lentzsch et al., Combination of bendamustine, lenalidomide, and dexamethasone (BLD) in patients with relapsed or refractory multiple myeloma is feasible and highly effective: results of phase ½ open-label, dose escalation study. Blood. May 17, 2012;119(20):4608-13.
Leoni et al., Bendamustine (Treanda) displays a distinct pattern of cytotoxicity and unique mechanistic features compared with other alkylating agents. Clin Cancer Res. Jan. 1, 2008;14(1):309-17.
Leoni, Bendamustine: rescue of an effective antineoplastic agent from the mid-twentieth century. Semin Hematol. Apr. 2011;48 Suppl 1:S4-11.
Leung-Hagesteijn et al., Xbpls-negative tumor B cells and pre-plasmablasts mediate therapeutic proteasome inhibitor resistance in multiple myeloma. Cancer Cell. Sep. 9, 2013;24(3):289-304.
Liby et al., Elevated and Deregulated Expression of HDAC3 in Human Astrocytic Glial Tumours. Folia Biologica (Praha). 2006;52:21-33.
Lin et al., Anti-rheumatic activities of histone deacetylase (HDAC) inhibitors in vivo in collagen-induced arthritis in rodents. Br J Pharmacol. Apr. 2007;150(7):862-72.
Lin et al., Treatment of Brain Metastases. J Clin Oncol. Oct. 20, 2015;33(30):3475-84.
Little et al., Experimental autoimmune vasculitis: an animal model of anti-neutrophil cytoplasmic autoantibody-associated systemic vasculitis. Am J Pathol. Apr. 2009;174(4):1212-20.
Little et al., Therapeutic effect of anti-TNF-alpha antibodies in an experimental model of anti-neutrophil cytoplasm antibody-associated systemic vasculitis. J Am Soc Nephrol. Jan. 2006;17(1):160-9.
Liu et al., A DNA/HDAC dual-targeting drug CY190602 with significantly enhanced anticancer potency. EMBO Mol Med. 12 pages, Published online: Mar. 9, 2015.
Liu, Characterization of TCL1-Tg:P53-/-Mice that Resemble Human Chronic Lymphocytic Leukemia with 17P-Deletion. UT GSBS Thesis, Graduate School of Biomedical Sciences, Digital Commons@The Texas Medical Center, May 2013. 142 pages.
Loftsson et al., Historical Perspectives: Cyclodextrins and their pharmaceutical applications. International Journal of Pharmaceutics. 2007;329:1-11.
Lombardi et al., Predictors of survival and effect of short (40 Gy) or standard-course (60 Gy) irradiation plus concomitant temozolomide in elderly patients with glioblastoma: a multicenter retrospective study of AINO (Italian Association of Neuro-Oncology). J Neurooncol. Nov. 2015;125(2):359-67.
Lopez-Iglesias et al., Preclinical anti-myeloma activity of EDO-S101, a new bendamustine-derived molecule with added HDACi activity, through potent DNA damage induction and impairment of DNA repair. J Hematol Oncol. Jun. 20, 2017;10(1):127. 14 pages.
Lopez-Iglesias et al., Preclinical anti-myeloma activity of the alkylating-HDACi molecule EDO-S101 through DNA-damaging and HDACi effects. EDO, http://mundipharma-edo.com. Poster Jun. 1, 2014.
Lopez-Iglesias et al., Preclinical Anti-Myeloma Activity of the Alkylating-HDACi Molecule EDO-S101 Through DNA-Damaging and HDACi Effects. EHA 2014 Poster, Jun. 12, 2014.
Lopez-Iglesias et al., Preclinical antimyeloma activity of EDO-S101 (bendamustine-vorinostat fusion molecule) through DNA-damaging and HDACi effects. 15th International Myeloma Workshop. Sep. 23-26, 2015. Rome, Italy. Clinical Lymphoma, Myeloma & Leukemia. Sep. 2015;15(3 Suppl. 3):e218, Abstract P0-238.
Lopez-Iglesias et al., The Alkylating Histone Deacetylase Inhibitor Fusion Molecule Edo-S101 Displays Full Bi-Functional Properties in Preclinical Models of Hematological Malignancies. Blood. 2014;124:2100.
Lopez-Iglesias et al., The Hybrid Molecule, Edo-S101, Impairs Double Strand Breaks Repair in Multiple Myeloma and Synergizes with Bortezomib and Dexamethasone. Blood. 2015;126(23):5354-5354.
Lucio-Eterovic et al., Differential expression of 12 histone deacetylase (HDAC) genes in astrocytomas and normal brain tissue: class II and IV are hypoexpressed in glioblastomas. BMC Cancer. Aug. 19, 2008;8:243.
Ludwig et al., Bendamustine-bortezomib-dexamethasone is an active and well-tolerated regimen in patients with relapsed or refractory multiple myeloma. Blood. Feb. 13, 2014;123(7):985-91.
Marchion et al., Development of histone deacetylase inhibitors for cancer treatment. Expert Rev Anticancer Ther. Apr. 2007;7(4):583-98.

(56) References Cited

OTHER PUBLICATIONS

Marks, Discovery and development of SAHA as an anticancer agent. Oncogene. Feb. 26, 2007;26(9):1351-6.
Marmion et al., Hydroxamic Acids—An Intriguing Family of Enzyme Inhibitors and Biomedical Ligands. Eur J Inorg Chem. 2004(15):3003-3016.
McInnis et al., Dysregulation of autoantigen genes in ANCA-associated vasculitis involves alternative transcripts and new protein synthesis. J Am Soc Nephrol. Feb. 2015;26(2):390-9.
Meanwell, Synopsis of some recent tactical application of bioisosteres in drug design. J Med Chem. Apr. 28, 2011;54(8):2529-91.
Medline AN—NLM24103869, Chen et al., Dexamethasone and Vorinostat Cooperatively Promote Differentiation and Apoptosis in Kasumi-1 Leukemia Cells Through Ubiquitination and Degradation of AML1-ETO. 2 pages, 2013.
Medline/NLM AN: NLM24998648, 1 page, 2014.
Mehrling et al., Activity of the alkylating histone-deacetylase inhibition fusion molecule EDO-S-101 in preclinical models of human glioblastoma independent from MGMT expression. Journal of Clinical Oncology. May 29, 2017;33(Suppl. 15), Abstract e13031.
Mehrling et al., Is there hope to treat glioblastoma effectively? CNS Oncol. 2015;4(6):377-9.
Mehrling et al., The Alkylating-HDAC Inhibition Fusion Principle: Taking Chemotherapy to the Next Level with the First in Class Molecule EDO-S101. Anticancer Agents Med Chem. 2016;16(1):20-8.
Mehrling, Chemotherapy is getting 'smarter'. Future Oncol. 2015;11(4):549-52.
Mehrling, First in human clinical trails to commence Q3 2015. Mundipharma EDO GmbH. Retrieved online at: http://mundipharma-edo.com. Jul. 31, 2015. 2 pages.
Mehrling, First-in-human clinical trial of its lead compound, EDO-S101. Mundipharma EDO GmbH. Retrieved online at: http://mundipharma-edo.com. May 31, 2016. 2 pages.
Mehrling, Fusion Therapy, a New Approach to Combining Treatments. Drug Discovery World. 2016;71-76.
Mey et al., Bendamustine, lenalidomide and dexamethasone (BRd) has high activity as 2(nd)-line therapy for relapsed and refractory multiple myeloma—a phase II trial. Br J Haematol. Mar. 2017;176(5):770-782.
Miller et al., Histone deacetylase inhibitors. J Med Chem. Nov. 20, 2003;46(24):5097-116.
Minucci et al., Histone deacetylase inhibitors and the promise of epigenetic (and more) treatments for cancer. Nat Rev Cancer. Jan. 2006;6(1):38-51.
Mishra et al., Histone deacetylase inhibitors modulate renal disease in the MRL-lpr/lpr mouse. J Clin Invest. Feb. 2003;111(4):539-52.
Moosman et al., Weekly treatment with a combination of bortezomib and bendamustine in relapsed or refractory indolent non-Hodgkin lymphoma. Leuk Lymphoma. Jan. 2010;51(1):149-52.
Moradei et al., Histone deacetylase inhibitors: latest developments, trends and prospects. Curr Med Chem Anticancer Agents. Sep. 2005;5(5):529-60.
Moreau et al., Phase 1b Dose Escalation Study Of Oral Quisinostat, a Histone Deacetylase Inhibitor (HDACi), In Combination With Velcade (Bortezomib) and Dexamethasone For Patients With Relapsed Multiple Myeloma (MM). Blood. Nov. 15, 2013;122(21):1932.
Moreau et al., Proteasome inhibitors in multiple myeloma: 10 years later. Blood. Aug. 2, 2012;120(5):947-59.
Moscovitch et al., Successful treatment of autoimmune manifestations in MRL/l and MRL/n mice using total lymphoid irradiation (TLI). Exp Mol Pathol. Feb. 1983;38(1):33-47.
Moskowitz et al., Phase II study of bendamustine in relapsed and refractory Hodgkin lymphoma. J Clin Oncol. Feb. 1, 2013;31(4):456-60.
Moskowitz, Bendamustine: a bridge to longer term solutions in heavily treated Hodgkin lymphoma. Leuk Lymphoma. Nov. 2013;54(11):2339-40.
MRF, Melanoma Research Foundation, Melanoma Central Nervous System Metastases, Current Approaches, Challenges and Opportunities. 5 pages (2015).
Munakata et al., The discovery and the development of bendamustine for the treatment of non-Hodgkin lymphoma. Expert Opin Drug Discov. Nov. 2016;11(11):1123-1130.
Munker et al., Activity of Tyrosine Kinase Inhibitors in Multiple Myeloma. Blood. 2007;110(11):274B, Abstract 4804.
National Institute of Health, Cancer. MedlinePlus. Retrieved online at: http://www.nlm.nih.gov/medlineplus/cancer.html. 10 pages. Apr. 16, 2007.
O'Donnell et al., Cancer pharmacoethnicity: ethnic differences in susceptibility to the effects of chemotherapy. Clin Cancer Res. Aug. 1, 2009;15(15):4806-14.
O'Reilly et al., Urinary Soluble CD163 in Active Renal Vasculitis. J Am Soc Nephrol. Sep. 2016;27(9):2906-16.
Ocio et al., Deacetylase Inhibition in Haematological Malignancies—Advanced T-cell Lymphoma, Hodgkin's Lymphoma, Multiple Myeloma, Acute Myelogenous Leukaemia and Myelodysplastic Syndrome. European Haematology. 2010;4:47-50.
Ocio et al., In vitro and in vivo rationale for the triple combination of panobinostat (LBH589) and dexamethasone with either bortezomib or lenalidomide in multiple myeloma. Haematologica. May 2010;95(5):794-803.
Ocio et al., Phase I study of plitidepsin in combination with bortezomib and dexamethasone in patients with relapsed and/or refractory multiple myeloma. Journal of Clinical Oncology. 2016;34 Abstract 8006, 1 page.
Ocio et al., Triple Combinations of the HDAC Inhibitor Panobinostat (LBH589) Plus Dexamethasone with Either Lenalidomide or Bortezomib are Highly Effective in a Multiple Myeloma Mouse Model. Blood. 2007;110:Abstract 1514. ASH Annual Meeting.
Ocio, Epigenetic regulation and HAC inhibitors, Still a role for these agents in MM? Institute of Biomedical Research of Salamanca, University of Salamanca, Cancer Research Center, Slideshow. 32 pages, (2016).
Offidani et al., Efficacy and tolerability of bendamustine, bortezomib and dexamethasone in patients with relapsed-refractory multiple myeloma: a phase II study. Blood Cancer J. Nov. 22, 2013;3:e162.
Ogura et al., A multicentre phase II study of vorinostat in patients with relapsed or refractory indolent B-cell non-Hodgkin lymphoma and mantle cell lymphoma. Br J Haematol. Jun. 2014;165(6):768-76.
Oken et al., Toxicity and response criteria of the Eastern Cooperative Oncology Group. Am J Clin Oncol. Dec. 1982;5(6):649-55.
Oriol et al., Outcome after relapse of acute lymphoblastic leukemia in adult patients included in four consecutive risk-adapted trials by the PETHEMA Study Group. Haematologica. Apr. 2010;95(4):589-596.
Paris et al., Histone deacetylase inhibitors: from bench to clinic. J Med Chem. Mar. 27, 2008;51(6):1505-29.
Phan et al., An update on ethnic differences in drug metabolism and toxicity from anti-cancer drugs. Expert Opin Drug Metab Toxicol. Nov. 2011;7(11):1395-410.
Phiel et al., Histone deacetylase is a direct target of valproic acid, a potent anticonvulsant, mood stabilizer, and teratogen. J Biol Chem. Sep. 28, 2001;276(39):36734-41.
Pitha et al., Parenteral hydroxypropyl cyclodextrins: intravenous and intracerebral administration of lipophiles. J Pharm Sci. Jun. 1994;83(6):833-7.
Poenisch et al., Bendamustine/Prednisone Versus Melphalane/Prednisone in the Primary Treatment of Multiple Myeloma: an Updated Analysis of the 94BP01 Protocol. Blood. 2000;96(Suppl 1:759a), Abstract 3284, Poster Board Session 748-111.
Puetzer et al., Towards novel strategies of targeting specific vulnerabilities of T-PLL cells. AACR Annual Meeting. Jul. 2017;77(Suppl 13), Abstract 1372.
Pönisch et al., Combined bendamustine, prednisone and bortezomib (BPV) in patients with relapsed or refractory multiple myeloma. J Cancer Res Clin Oncol. Mar. 2013;139(3):499-508.
Pönisch et al., Treatment of bendamustine and prednisone in patients with newly diagnosed multiple myeloma results in superior complete response rate, prolonged time to treatment failure and improved

(56) References Cited

OTHER PUBLICATIONS quality of life compared to treatment with melphalan and prednisone—a randomized phase III study of the East German Study Group of Hematology and Oncology (OSHO). J Cancer Res Clin Oncol. Apr. 2006;132(4):205-12.

Qian et al., Activity of PXD101, a histone deacetylase inhibitor, in preclinical ovarian cancer studies. Mol Cancer Ther. Aug. 2006;5(8):2086-95.

Rajewski et al., Preliminary safety evaluation of parenterally administered sulfoalkyl ether beta-cyclodextrin derivatives. J Pharm Sci. Aug. 1995;84(8):927-32.

Rang et al., Glucocorticoids. Rang and Dale's Pharmacology, Sixth Edition. Elsevier, Limited, 3 pages, (2007).

Rasheed et al., Histone deacetylase inhibitors in cancer therapy. Expert Opin Investig Drugs. May 2007;16(5):659-78.

Rasschaert et al., A phase I study of bendamustine hydrochloride administered day 1+2 every 3 weeks in patients with solid tumours. Br J Cancer. Jun. 4, 2007;96(11):1692-8.

Rasschaert et al., A phase I study of bendamustine hydrochloride administered once every 3 weeks in patients with solid tumors. Anticancer Drugs. Jun. 2007;18(5):587-95.

Regna et al., HDAC expression and activity is upregulated in diseased lupus-prone mice. Int Immunopharmacol. Dec. 2015;29(2):494-503.

Reilly et al., Modulation of renal disease in MRL/lpr mice by suberoylanilide hydroxamic acid. J Immunol. Sep. 15, 2004;173(6):4171-8.

Rengstl et al., Small and big Hodgkin-Reed-Sternberg cells of Hodgkin lymphoma cell lines L-428 and L-1236 lack consistent differences in gene expression profiles and are capable to reconstitute each other. PLoS One. May 15, 2017;12(5):e0177378.

Richardson et al., Panorama 2: panobinostat in combination with bortezomib and dexamethasone in patients with relapsed and bortezomib-refractory myeloma. Blood. Oct. 3, 2013;122(14):2331-7.

Rodriguez-Tenreiro Y Sanchez, Hydrogels of Cyclodextrin Co-crosslinked and Interpenetrated for Controlled Drug Release. University of Santiago de Compostela, School of Pharmacy. pp. 29-32, (2006).

Ryu et al., Valproic acid downregulates the expression of MGMT and sensitizes temozolomide-resistant glioma cells. J Biomed Biotechnol. 2012;2012:987495. 9 pages.

Sampson et al., Vorinostat Enhances Cytotoxicity of SN-38 and Temozolomide in Ewing Sarcoma Cells and Activates STAT3/AKT/MAPK Pathways. PLoS One. Nov. 16, 2015;10(11):e0142704, 19 pages.

Sanchez et al., Anti-Myeloma Effects of Carfilzomib with Cyclophosphamide (CY) or Bendamustine (Ben). Blood. 2012;120(21), Abstract 2952. 54th ASH Annual Meeting adn Exposition.

Santacruz et al., The prognostic impact of minimal residual disease in patients with chronic lymphocytic leukemia reguiring first-line therapy. Haematologica. May 2014;99(5):873-80.

Sarkaria et al., Mechanisms of chemoresistance to alkylating agents in malignant glioma. Clin Cancer Res. May 15, 2008;14(10):2900-8.

Saulnier et al., An Efficient Method for the Synthesis of Guanidino Prodrugs. Bioorganic & Medicinal Chemistry Letters. 1994;4(16):1985-1990.

Sawas et al., The Combination of Brentuximab Vedotin (Bv) and Bendamustine (B) Demonstrates Marked Activity in Heavily Treated Patients with Relapsed or Refractory Hodgkin Lymphoma (HL) and Anaplastic Large T-Cell Lymphoma (ALCL): Results of an International Multi Center Phase I/II Experience. Blood. 2015;126:586.

Schöffski et al., Repeated administration of short infusions of bendamustine: a phase I study in patients with advanced progressive solid tumours. J Cancer Res Clin Oncol. Jan. 2000;126(1):41-7.

Schöffski et al., Weekly administration of bendamustine: a phase I study in patients with advanced progressive solid tumours. Ann Oncol. Jun. 2000;11(6):729-34.

Shah et al., Comprehensive analysis of MGMT promoter methylation: correlation with MGMT expression and clinical response in GBM. PLoS One. Jan. 7, 2011;6(1):e16146.

Shipley et al., Acute myelogenous leukemia. Exp Hematol. Jun. 2009;37(6):649-58.

Simon, Optimal two-stage designs for phase II clinical trials. Control Clin Trials. Mar. 1989;10(1):1-10.

Song et al., Increased expression of histone deacetylase 2 is found in human gastric cancer. APMIS. 2005;113:264-8.

Stiborová et al., The synergistic effects of DNA-targeted chemotherapeutics and histone deacetylase inhibitors as therapeutic strategies for cancer treatment. Curr Med Chem. 2012;19(25):4218-38.

Storer, Design and analysis of phase I clinical trials. Biometrics. Sep. 1989;45(3):925-37.

Sturn et al., Genesis: cluster analysis of microarray data. Bioinformatics. Jan. 2002;18(1):207-8.

Tago et al., Repeated 0.5-Gy gamma irradiation attenuates autoimmune disease in MRL-lpr/lpr mice with suppression of CD3+CD4−CD8−B220+ T-cell proliferation and with up-regulation of CD4+CD25+Foxp3+ regulatory T cells. Radiat Res. Jan. 2008;169(1):59-66.

Takai et al., Human ovarian carcinoma cells: histone deacetylase inhibitors exhibit antiproliferative activity and potently induce apoptosis. Cancer. Dec. 15, 2004;101(12):2760-70.

Tesar et al., Limitations of standard immunosuppressive treatment in ANCA-associated vasculitis and lupus nephritis. Nephron Clin Pract. 2014;128(3-4):205-15.

Thurn et al., Rational therapeutic combinations with histone deacetylase inhibitors for the treatment of cancer. Future Oncol. Feb. 2011;7(2):263-83.

Topalian et al., Immune checkpoint blockade: a common denominator approach to cancer therapy. Cancer Cell. Apr. 13, 2015;27(4):450-61.

Trivedi et al., Management of Chemotherapy-Induced Peripheral Neuropathy. American Journal of Hematology / Oncology. Jan. 2015;11(1):4-10.

Tutt et al., Oral poly(ADP-ribose) polymerase inhibitor olaparib in patients with BRCA1 or BRCA2 mutations and advanced breast cancer: a proof-of-concept trial. Lancet. Jul. 24, 2010;376(9737):235-44.

Valdez et al., Synergistic cytotoxicity of the DNA alkylating agent busulfan, nucleoside analogs and suberoylanilide hydroxamic acid in lymphoma cell lines. Leuk Lymphoma. May 2012;53(5):973-81.

Van Krieken, New developments in the pathology of malignant lymphoma. A review of the literature published from Jan.-Apr. 2016. J Hematop. Jun. 13, 2016;9(2):73-83.

Viel et al., Optimizing glioblastoma temozolomide chemotherapy employing lentiviral-based anti-MGMT shRNA technology. Mol Ther. Mar. 2013;21(3):570-9.

Vippagunta et al., Crystalline Solids. Advanced Drug Delivery Reviews. 2001;48:3-26.

Vlachostergios et al., Bortezomib overcomes MGMT-related resistance of glioblastoma cell lines to temozolomide in a schedule-dependent manner. Invest New Drugs. Oct. 2013;31(5):1169-81.

Von Tresckow et al., An update on emerging drugs for Hodgkin lymphoma. Expert Opin Emerg Drugs. Jun. 2014;19(2):215-24.

Vyas et al., Cyclodextrin based novel drug delivery systems. J Incl Phenom Macrocycl Chem. 2008;62:23-42.

Wang et al., Effect of histone deacetylase inhibitor NL101 on rat neurons. Zhejiang Da Xue Bao Yi Xue Ban. May 2014;43(3):265-272. Abstract Only. 2 pages.

Wang et al., Independent validation of a model using cell line chemosensitivity to predict response to therapy. J Natl Cancer Inst. Sep. 4, 2013; 105(17):1284-91.

Wang et al., Phase 1 trial of linifanib (ABT-869) in patients with refractory or relapsed acute myeloid leukemia. Leuk Lymphoma. Aug. 2012;53(8):1543-51.

Wang et al., Toward selective histone deacetylase inhibitor design: homology modeling, docking studies, and molecular dynamics simulations of human class I histone deacetylases. J Med Chem. Nov. 3, 2005;48(22):6936-47.

(56) References Cited

OTHER PUBLICATIONS

Watanabe et al., Modulation of renal disease in MRL/lpr mice genetically deficient in the alternative complement pathway factor B. J Immunol. Jan. 15, 2000;164(2):786-94.

Weil et al., Breast cancer metastasis to the central nervous system. Am J Pathol. Oct. 2005;167(4):913-20.

Wiegmans et al., Differences in Expression of Key DNA Damage Repair Genes after Epigenetic-Induced BRCAness Dictate Synthetic Lethality with PARP1 Inhibition. Mol Cancer Ther. Oct. 2015;14(10):2321-31.

Wilson et al., Histone deacetylase 3 (HDAC3) and other class I HDACs regulate colon cell maturation and p21 expression and are deregulated in human colon cancer. J Biol Chem. May 12, 2006;281(19):13548-58.

Wilson et al., Relationship of p53, bcl-2, and tumor proliferation to clinical drug resistance in non-Hodgkin's lymphomas. Blood. Jan. 15, 1997;89(2):601-9.

Witzel et al., Long-term tumor remission under trastuzumab treatment for HER2 positive metastatic breast cancer—results from the HER-OS patient registry. BMC Cancer. Nov. 4, 2014;14:806. 7 pages.

Xiao et al., Antineutrophil cytoplasmic autoantibodies specific for myeloperoxidase cause glomerulonephritis and vasculitis in mice. J Clin Invest. Oct. 2002;110(7):955-63.

Xie et al., Quantitative structure-activity relationship study of histone deacetylase inhibitors. Curr Med Chem Anticancer Agents. May 2004;4(3):273-99.

Yan et al., Synergistic Inhibition of Tumor Growth and Overcoming Chemo-Resistance by Simultaneously Targeting Key Components in DNA Damage/Repair, Epigenetic, and Putative Cancer Stem Cell Signaling Pathways Using Novel Dual-Functional DNA-Alkylating/HDAC Inhibitor and Tumor Suppressor Gene Nanoparticles in Cancer Research. Cancer Research. Apr. 15, 2012;72(8, Suppl. 1) Proceedings: AACR 103rd Annual Meeting. Abstract 2741. 2 pages.

Yardley, Drug resistance and the role of combination chemotherapy in improving patient outcomes. Int J Breast Cancer. 2013;2013:137414. 15 pages.

Zaja et al., Bendamustine salvage therapy for T cell neoplasms. Ann Hematol. Sep. 2013;92(9):1249-54.

Zhang et al., A novel suberoylanilide hydroxamic acid histone deacetylase inhibitor derivative, N25, exhibiting improved antitumor activity in both human U251 and H460 cells. Asian Pac J Cancer Prev. 2014;15(10):4331-8.

Zhu et al., Histone deacetylase 3 implicated in the pathogenesis of children glioma by promoting glioma cell proliferation and migration. Brain Res. Jul. 3, 2013;1520:15-22.

Zinzani et al., Brentuximab Vedotin in Transplant-Naïve Relapsed/Refractory Hodgkin Lymphoma: Experience in 30 Patients. Oncologist. Dec. 2015;20(12):1413-6.

Zulkowski et al., Regression of brain metastases from breast carcinoma after chemotherapy with bendamustine. J Cancer Res Clin Oncol. Feb. 2002;128(2):111-3.

Baker et al., Investigation of bendamustine HCL in a phase 2 study in women with resistant ovarian cancer. Invest New Drugs. Feb. 2013;31(1):160-6.

Bender, Across the divide The blood-brain barrier represents a formidable obstacle for cancer drugs. Nature. Sep. 27, 2018;561:S46-S47.

Chavez et al., Triple negative breast cancer cell lines: one tool in the search for better treatment of triple negative breast cancer. Breast Dis. 2010;32(1-2):35-48.

Chen et al., Dexamethasone and vorinostat cooperatively promote differentiation and apoptosis in Kasumi-1 leukemia cells through ubiquitination and degradation of AML1-ETO. Zhonghua Xue Ye Xue Za Zhi. Sep. 2013;34(9):741-4.

ClinicalTrials.gov, Study of EDO-S101, A First-in-Class Alkylating HDACi Fusion Molecule, in Relapsed/Refractory Hematologic Malignancies. ClinicalTrials.gov Identifier: NTC02576496, 4 pages, Oct. 2015.

ClinicalTrials.gov, Study of the Safety, Pharmacokinetics and Efficacy of EDO-S101, in Patients With Advanced Solid TumorsClinical Trials Identifier: NCT03345485, Dec. 24, 2020. 12 pages.

De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Blood. 2015;126(23):2479. 7 pages.

De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. Blood. 2015;126:2481, 5 pages.

Detich et al., Valproate induces replication-independent active DNA demethylation. J Biol Chem. Jul. 25, 2003;278(30):27586-92.

Formenti et al., Results of a phase I-II study of adjuvant concurrent carboplatin and accelerated radiotherapy for triple negative breast cancer. Oncoimmunology. Dec. 27, 2016;6(3):e1274479, 8 pages.

Gravina et al., The novel CXCR4 antagonist, PRX177561, reduces tumor cell proliferation and accelerates cancer stem cell differentiation in glioblastoma preclinical models. Tumor Biology. Jun. 2017;1-17.

Guntner et al., Cerebrospinal fluid penetration of targeted therapeutics in pediatric brain tumor patients. Acta Neuropathol Commun. Jun. 3, 2020;8(1):78, 13 pages.

Hartmann et al., Bendamustine hydrochloride in patients with refractory soft tissue sarcoma: a noncomparative multicenter phase 2 study of the German sarcoma group (AIO-001). Cancer. Aug. 15, 2007;110(4):861-6.

Herbaux et al., Bendamustine is effective in T-cell prolymphocytic leukaemia. Br J Haematol. Mar. 2015;168(6):916-9.

Hummel et al., A pediatric phase 1 trial of vorinostat and temozolomide in relapsed or refractory primary brain or spinal cord tumors: a Children's Oncology Group phase 1 consortium study. Pediatr Blood Cancer. Sep. 2013;60(9);1452-7.

Koster et al., Carboplatin in Combination with Bendamustine in Previously Untreated Patients with Extensive-Stage Small Cell Lung Cancer (SCLC). Clin Drug Investig. 2004;24(10):611-8.

Li et al., Pharmacokinetics of bendamustine in the central nervous system: chemoinformatic screening followed by validation in a murine model. MedChemComm. 2012;3:1526-1530.

Liu et al., Effects of suberoylanilide hydroxamic acid (SAHA) combined with paclitaxel (PTX) on paclitaxel-resistant ovarian cancer cells and insights into the underlying mechanisms Cancer Cell Int. Nov. 26, 2014;14(1):112, 11 pages.

Loibl et al., Multicenter Phase II Study with Weekly Bendamustine and Paclitaxel as First- or Later-Line Therapy in Patients with Metastatic Breast Cancer: RiTa II Trial. Breast Care (Basel). Dec. 2011,6(6):457-461.

Lopez-Iglesias et al., Preclinical anti-myeloma activity of the alkylating-HDACi Fusion Molecule EDO-S101 Through DNA-damaging and HDACi Effects. Haematologica. 2014;99(s1):354-355, Abstract P942.

Mehrling, Mundipharma EDO GmbH Announces FDA Investigational New Drug Approval of its First anti-Cancer Compound, EDO-S101, for the Treatment of Patients with Relapsed/Refractory Haematologic Malignancies and Solid Tumours. EDO, http://mundipharma-edo.com/2015/07/31/mundipharma-edo-gmbh-announces-fda-investigational-new-drug-approval-of-its-first-anti-cancer-compound-edo-s101-for-the-treatment-of-patients-with-relapsedrefractory-haematologic-malignancies-and-s/. 2 pages, Jul. 31, 2015.

Mehrling, Mundipharma EDO GmbH announces first-in-human clinical trial of its lead compound, EDO-S101. EDO, http://mundipharma-edo.com/2016/07/20/mundipharma-edo-gmbh-announces-first-in-human-clinical-trial-of-lead-compound-edo-s101/. 2 pages, May 31, 2016.

Min et al., Histone deacetylase inhibitor, suberoylanilide hydroxamic acid (SAHA), enhances anti-tumor effects of the poly (ADP-ribose) polymerase (PARP) inhibitor olaparib in triple-negative breast cancer cells. Breast Cancer Res. Mar. 7, 2015;17:33, 13 pages.

Oi et al., Synergistic induction of NY-ESO-1 antigen expression by a novel histone deacetylase inhibitor, valproic acid, with 5-aza-2'-deoxycytidine in glioma cells. J Neurooncol. Mar. 2009;92(1):15-22.

(56) References Cited

OTHER PUBLICATIONS

Rang et al., Rang and Dale's Pharmacology, Sixth Edition. Churchill Livingstone Elsevier. Chapter 51, p. 729, (2007).

Reagan-Shaw et al., Dose translation from animal to human studies revisited. FASEB J. Mar. 2008;22(3):659-61.

Serra et al., Co-clinical trial of olaparib in breast and ovarian patient-derived tumor xenografts (PDX) enables the identification of response biomarkers. Clin Cancer Res. 2016;22(Suppl 16):Abstract B02, 4 pages.

Siegel et al., Vorinostat in combination with lenalidomide and dexamethasone in patients with relapsed or refractory multiple myeloma. Blood Cancer J. Feb. 21, 2014;4(2):e182, 6 pages.

Tsai et al., Valproic Acid Enhanced Temozolomide-Induced Anticancer Activity in Human Glioma Through the p53-PUMA Apoptosis Pathway. Front Oncol. Oct. 1, 2021;11:722754, 13 pages.

Tseng et al., A comparison of the molecular subtypes of triple-negative breast cancer among non-Asian and Taiwanese women. Breast Cancer Res Treat. Jun. 2017;163(2):241-254.

Vlachostergios et al., Bortezomib downregulates MGMT expression in T98G glioblastoma cells. Cell Mol Neurobiol. Apr. 2013;33(3):313-8.

White, FDA accepts Mundipharma EDO's IND for EDO-S101. European Pharmaceutical Review. 4 pages, Aug. 3, 2015.

Wikipedia, Triple-negative breast cancer. Retrieved online at: https://en.wikipedia.org/wiki/Triple-negative_breast_cancer. 7 pages, Feb. 20, 2017.

Zhao et al., Comparison of methods for evaluating drug-drug interaction. Front Biosci (Elite Ed). Jan. 1, 2010;2:241-9.

Zinzani et al., Dose Escalation of Tinostamustine in Patients with Relapsed/Refractory (R/R) Lymphoid Malignancies. Retrieved online at: https://library.ehaweb.org/eha/2019/24th/266100/delphine.remmy.dose.escalation.of.tinostamustine.in.patients.with.relapsed.html?f=listing=3*browseby=8*sortby=1*media=1. 1 page, poster presentation. Jun. 1, 2019.

U.S. Appl. No. 13/143,155, filed Jul. 1, 2011, U.S. Pat. No. 8,609,864, Issued.
U.S. Appl. No. 14/075,145, filed Nov. 8, 2013, U.S. Pat. No. 9,096,627, Issued.
U.S. Appl. No. 14/972,750, filed Dec. 17, 2015, RE46,144, Issued.
U.S. Appl. No. 14/345,562, filed Nov. 3, 2014, U.S. Pat. No. 9,376,395, Issued.
U.S. Appl. No. 14/374,995, filed Jul. 28, 2014, U.S. Pat. No. 10,118,901, Issued.
U.S. Appl. No. 15/290,546, filed Oct. 11, 2016, 2018-0098969, Abandoned.
U.S. Appl. No. 15/314,162, filed Nov. 28, 2016, 2017-0151218, Abandoned.
U.S. Appl. No. 15/985,097, filed May 21, 2018, U.S. Pat. No. 10,406,138, Issued.
U.S. Appl. No. 16/517,936, filed Jul. 22, 2016, 2019-034807, Abandoned.
U.S. Appl. No. 15/314,167, filed Nov. 28, 2016, U.S. Pat. No. 9,993,482, Abandoned.
U.S. Appl. No. 15/314,172, filed Nov. 28, 2016, 2017-0189382, Published.
U.S. Appl. No. 15/314,180, filed Nov. 28, 2016, U.S. Pat. No. 10,744,120, Issued.
U.S. Appl. No. 16/983,458, filed Aug. 3, 2020, Abandoned.
U.S. Appl. No. 16/994,154, filed Aug. 14, 2020, 2021-0059989, Published.
U.S. Appl. No. 16/341,089, filed Apr. 11, 2019, U.S. Pat. No. 11,266,631, Issued.
U.S. Appl. No. 17/679,308, filed Feb. 24, 2022, Pending.
U.S. Appl. No. 16/621,885, filed Dec. 12, 2019, 2020-0113870, Published.
U.S. Appl. No. 16/621,893, filed Dec. 12, 2019, 2020-0261423, Published.
U.S. Appl. No. 16/621,896, filed Dec. 12, 2019, 2020-0230109, Published.
U.S. Appl. No. 16/621,898, filed Dec. 12, 2019, U.S. Pat. No. 11,318,117, Issued.
U.S. Appl. No. 17/730,276, filed Apr. 27, 2022, Pending.
U.S. Appl. No. 17/414,797, filed Jun. 16, 2021, 2022-0016084, Published.
U.S. Appl. No. 17/414,806, filed Jun. 16, 2021, 2022-0016085, Published.

Bijnsdorp et al., Analysis of Drug Interactions. Cancer Cell Culture, Methods and Protocols, Second Edition, Methods in Molecular Biology, vol. 731. Ian A. Cree (Ed.), Humana Press. Chapter 34, pp. 421-434, (2011).

Gemmill et al., Synergistic growth inhibition by Iressa and Rapamycin is modulated by VHL mutations in renal cell carcinoma. Br J Cancer. Jun. 2, 20050;92(12):2266-77.

Palmer et al., Combination Cancer Therapy Can Confer Benefit via Patient-to-Patient Variability without Drug Additivity or Synergy Cell. Dec. 14, 2017;171(7):1678-1691.

PHARMACEUTICAL COMBINATIONS FOR TREATING CANCER

CROSS-REFERENCE TO RELATED APPLICATIONS

This application is a continuation application of U.S. patent application Ser. No. 16/517,936, filed on Jul. 22, 2019, which is a continuation of U.S. patent application Ser. No. 15/985,097, filed on May 21, 2018, now U.S. Pat. No. 10,406,138, which is a continuation of U.S. patent application Ser. No. 15/314,162, filed on Nov. 28, 2016, which is a U.S. national stage filing under 35 U.S.C. § 371(c), of International Application No. PCT/EP2015/061571, filed on May 26, 2015, which claims foreign priority of U.K. Patent Application No. 1409471.8, filed on May 28, 2014. The entire contents of each of the aforementioned applications, including original claims and drawings, are incorporated herein by reference.

TECHNICAL FIELD

The present invention relates to combinations and compositions that are of use in the treatment of cancer, for example in the treatment of breast cancer or of hematologic cancers such as multiple myeloma, lymphoma or leukemia.

BACKGROUND TO THE INVENTION

Cancer is one of the most life threatening diseases. Cancer is a condition in which cells in a part of the body experience out-of-control growth. According to latest data from American Cancer Society, it is estimated there will be 1.67 million new cases of cancer in USA in 2014. Cancer is the second leading cause of death in the United States (second only to heart disease) and will claim more than 585,000 lives in 2014. In fact, it is estimated that 50% of all men and 33% of all women living in the United States will develop some type of cancer in their lifetime. Therefore cancer constitutes a major public health burden and represents a significant cost in the United States. These figures are reflected elsewhere across most countries globally, although the types of cancer and relative proportions of the population developing the cancers vary depending upon many different factors such including genetics and diet.

For decades surgery, chemotherapy, and radiation were the established treatments for various cancers. Patients usually receive a combination of these treatments depending upon the type and extent of their disease. But chemotherapy is the most important option for cancer patients when surgical treatment (i.e. the removal of diseased tissue) is impossible. While surgery is sometimes effective in removing tumors located at certain sites, for example, in the breast, colon, and skin, it cannot be used in the treatment of tumors located in other areas, such as the backbone, nor in the treatment of disseminated hematologic cancers include cancers of the blood and blood-forming tissues (such as the bone marrow). They include multiple myeloma, lymphoma and leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism. It is used most often in the treatment of breast, lung, and testicular cancer. One of the main causes of failure in this treatment of cancer is the development of drug resistance by the cancer cells, a serious problem that may lead to recurrence of disease or even death. Thus, more effective cancer treatments are needed.

Multiple myeloma is a significant and growing problem. It is a cancer arising from plasma cells. Normal plasma cells produce immunoglobulins to fight infection. In myeloma, the plasma cells become abnormal, multiply uncontrollably and release only one type of anttibody—known as paraprotein—which has no useful function. It tends to accumulate in the bone marrow and circulate in the blood and can be detected in the urine as well. It affects multiple sites in the body (hence 'multiple' myeloma) where bone marrow is normally active in adults. The main forms of multiple myeloma (or myeloma as it is also referred to) are active myeloma, plasmacytoma, light chain myeloma and non-secretory myeloma. The number of new cases of myeloma in the US in 2011 was 6.1 per 100,000 men and women per year and the percentage survival rate beyond five years was 45%. It is estimated that the number of new cases in the US in 2014 will be over 24,000 (1.4% of all cancer cases), while the number of deaths in 2014 will be just over 11,000 (1.9% of all cancer cases).

In WO-A-2010/085377, the compound of formula I was shown to have excellent in vitro activity against multiple myeloma cell lines, with activities in the range of ×35-100 greater than the activity shown by bendamustin.

Leukemia is a type of cancer of the blood or bone marrow characterized by an abnormal increase of immature white blood cells called "blasts". Instead of producing normal, functioning white blood cells to fight infection the body produces large numbers of these non-functional blasts. Leukemia is a broad term covering a spectrum of diseases. In turn, it is part of the even broader group of diseases affecting the blood, bone marrow and lymphoid system, which are all known as hematological neoplasms. The most common forms are acute lymphoblastic leukemia (ALL), chronic lymphocytic leukemia (CLL), acute myeloid leukemia (AML) and chronic myeloid leukemia (CML), with less common forms including hairy cell leukemia (HCL), T-cell prolymphocytic leukemia (T-PLL), large granular lymphocytic leukemia and T-cell acute lymphoblastic leukemia. It is estimated that the number of new cases in the United States in 2014 will be over 52,000 (3.1% of all new cancers in the US) with over 24,000 deaths (4.1% of all cancer deaths in the US). The percentage survival rate over five years is currently 57.2%, a figure significantly lower than for many other cancers, with the survival rate over five years for acute myeloid leukemia being particularly low at only 20%.

Lymphoma is a cancer of the lymphatic system. There are two main types of lymphoma, namely Hodgkin lymphoma and non Hodgkin lymphoma.

Non Hodgkin lymphoma is the more common form of lymphoma. The lymphatic system runs throughout the body, and it is therefore possible to find non Hodgkin lymphoma in almost all parts of the body. In patients with non Hodgkin lymphoma, some of their white blood cells (lymphocytes) divide abnormally. They do not have any resting time like normal cells and they start to divide continuously, so too many are produced. They do not naturally die off as they usually do. These cells start to divide before they are fully mature and therefore cannot fight infection as normal white blood cells do. All the abnormal lymphocytes start to collect in the lymph nodes or other places such as the bone marrow or spleen. They can then grow into tumours and begin to cause problems within the lymphatic system or the organ in which they are growing. For example, if a lymphoma starts in the thyroid gland it can affect the normal production of thyroid hormones. There are many different types of non Hodgkin lymphoma. They can be classified in several different ways. One way is by the type of cell affected. In non Hodgkin lymphoma two types of lymphocyte can be affected—B cells and T cells. This is classified as B cell lymphoma or a T cell lymphoma. Most people with non Hodgkin lymphoma have B cell lymphomas. T cell lymphomas are more common in teenagers and young adults.

The cells of Hodgkin lymphoma have a particular appearance under the microscope. These cells are called Reed Sternberg cells. Non Hodgkin lymphomas do not have Reed Sternberg cells. It is important for doctors to be able to tell the difference between Hodgkin lymphoma and non Hodgkin lymphoma cells as they are two different diseases. In Hodgkin lymphoma, it is cells in the lymph nodes that have become cancerous.

The % survival rate over 5 years in 2009 for patients with non Hodgkin lymphoma was 63%, while the survival rate for those with Hodgkin lymphoma over the same period was 83%.

Breast cancer is a cancer that forms in tissues of the breast. The most common type of breast cancer is ductal carcinoma, which begins in the lining of the milk ducts (thin tubes that carry milk from the lobules of the breast to the nipple). Another type of breast cancer is lobular carcinoma, which begins in the lobules (milk glands) of the breast. Breast cancers can be classified into sub-groups as claudin-low tumors, basal-like tumors, human epidermal growth factor receptor 2 (HER2) positive tumors, luminal A tumors and luminal B tumors. Invasive breast cancer is breast cancer that has spread from where it began in the breast ducts or lobules to surrounding normal tissue. Breast cancer occurs in both men and women, although male breast cancer is rare. In 2014, it is estimated that there will be nearly 233,00 new cases in women and 2,400 in men, with 4,000 female deaths and just over 400 male deaths.

Approximately 15 out of every 100 women with breast cancer have triple-negative breast cancer, i.e. are estrogen negative, are progesterone negative and are HER2 negative. Recurrent triple-negative breast cancer is a condition of high unmet medical need, due to its aggressive biology, fast development of drug resistance and lack of molecular targets. Until now, chemotherapy remains the standard of care for advanced triple-negative breast cancer with a poor median overall survival.

In WO-A-2010/085377, the compound of formula I below is disclosed. It is a first-in-class dual-functional alkylating-HDACi fusion molecule which potently inhibits the HDAC pathway.

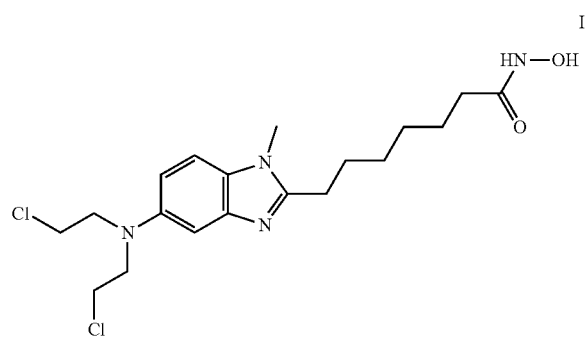 [SMILES: Cn1c(CCCCCCC(=O)NO)nc2cc(N(CCCl)CCCl)ccc21]

Biological assays showed that the compound of formula I potently inhibits HDAC enzyme (HDAC1 $IC_{50}$ of 9 nM) and it has been shown to have excellent in vitro activity against multiple myeloma cell lines.

There is a need for more effective cancer treatments, including the treatment of breast cancer and of hematologic cancers such as multiple myeloma, lymphoma or leukemia. Currently, these conditions affect many people and the medium to long-term prognosis is not good for many of these conditions.

SUMMARY OF THE INVENTION

In a first aspect of the present invention there is provided a combination comprising a proteasome inhibitor and a compound of formula I or a pharmaceutically acceptable salt thereof:

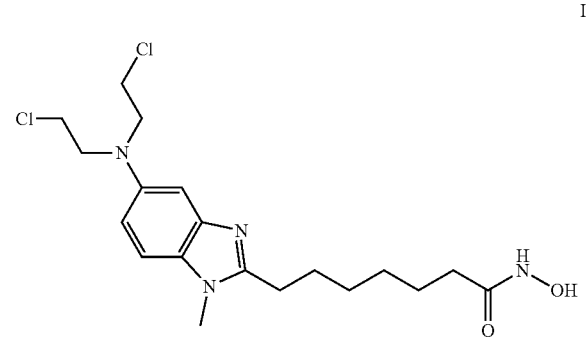 [SMILES: Cn1c(CCCCCCC(=O)NO)nc2cc(N(CCCl)CCCl)ccc21]

It has surprisingly been discovered that combinations of a compound of formula I or a pharmaceutically acceptable salt thereof and a proteasome inhibitor such as carfilzomib or bortezomib are particularly effective in the treatment of cancers including hematologic cancers such as multiple myeloma, lymphoma and leukemia, and breast cancer, such that they are highly promising in efforts to address the problem of finding more effective treatments for cancer. The combinations may optionally further comprise a glucocorticoid such as dexamethasone. These further combinations are also particularly effective in the treatment of cancer.

In a second aspect of the present invention, there is provided a pharmaceutical composition comprising a pharmaceutically acceptable diluent or carrier and a combination according to the first aspect of the invention.

In a third aspect of the present invention, there is provided a kit comprising a combination according to the first aspect of the present invention and, optionally, instructions for treating a patient.

In a fourth aspect of the present invention, there is provided a combination, composition or kit according to the first, second or third aspect of the present invention for use in the treatment of cancer.

In a fifth aspect of the present invention, there is provided a method of treating cancer in a patient in need thereof comprising administering to said patient a combination, composition or kit according to the first, second or third aspect of the present invention.

In a sixth aspect of the present invention, there is provided a compound of formula (I) or a pharmaceutically acceptable salt thereof for use in the treatment of relapsed/refractory multiple myeloma. In one embodiment, the compound of formula (I) or the pharmaceutically acceptable salt thereof is for use in the treatment of relapsed/refractory multiple myeloma in combination with a proteasome inhibitor and optionally further in combination with a glucocorticoid.

In a seventh aspect of the present invention, there is provided a method of treatment of relapsed/refractory multiple myeloma in a patient in need thereof comprising administering to said patient a compound of formula (I) or the pharmaceutically acceptable salt thereof. In one embodiment, the compound of formula (I) or the pharmaceutically acceptable salt thereof is administered in combination with a proteasome inhibitor and may further optionally be administered in combination with a glucocorticoid as well.

DETAILED DESCRIPTION OF THE INVENTION

Figure 1:
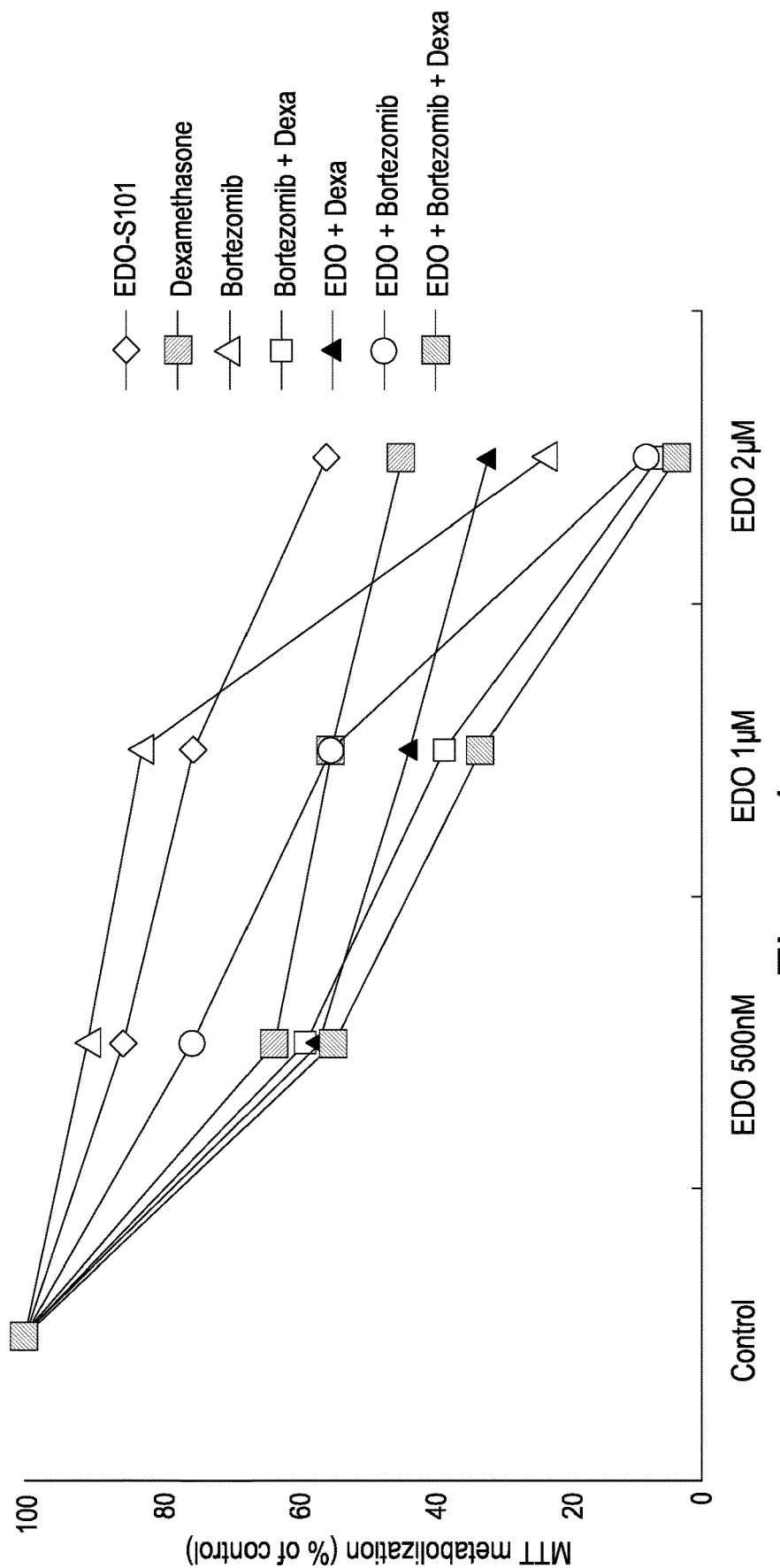
FIG. 1 is a plot of the % surviving in vitro MM1S multiple myeloma cells as a % of control versus concentration for different tested compounds after 48 hours incubation, for single compounds and as combinations (double and triple)

In the present application, a number of general terms and phrases are used, which should be interpreted as follows.

"Animal" includes humans, non-human mammals (e.g., dogs, cats, rabbits, cattle, horses, sheep, goats, swine, deer, and the like) and non-mammals (e.g., birds, and the like).

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulfate, bisulfate, sulfamate, nitrate, phosphate, and organic acid addition salts such as, for example, acetate, trifluoroacetate, maleate, fumarate, citrate, oxalate, succinate, tartrate, salicylate, tosylate, lactate, naphthalenesulphonae, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

It has surprisingly been discovered that combinations of a compound of formula I or a pharmaceutically acceptable salt thereof and a proteasome inhibitor such as carfilzomib or bortezomib are particularly effective in the treatment of cancers including hematologic cancers such as multiple myeloma, leukemia and lymphoma, and breast cancer such that they are highly promising in efforts to address the problem of finding more effective treatments for cancer. The combinations may optionally further comprise a glucocorticoid such as dexamethasone. These further combinations are also particularly effective in the treatment of cancer.

In the combination of the present invention, the pharmaceutically acceptable salt of the compound of formula I may preferably be the hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate or acetate, and more preferably the acetate.

In the combination of the present invention, the proteasome inhibitor may preferably be selected from the group consisting of bortezomib, carfilzomib, marizomib, delanzomib (CEP-18770), oprozomib (ONX 0912), ixazomib (MLN-9708) and LU-102, or a pharmaceutically acceptable salt thereof. Particularly preferably, the proteasome inhibitor may be selected from bortezomib, carfilzomib and LU-102.

The structures of these proteasome inhibitors are as follows:

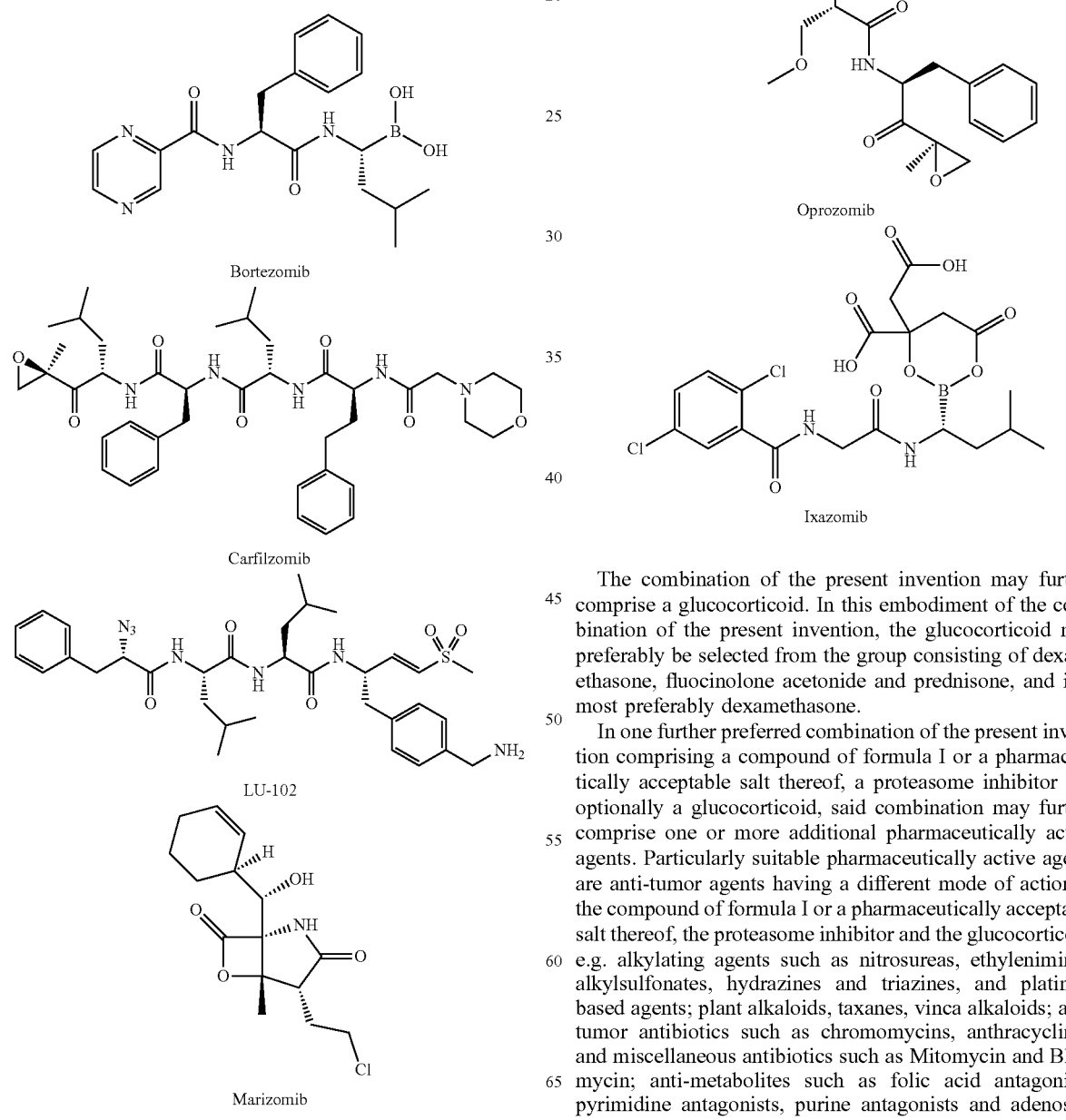

The combination of the present invention may further comprise a glucocorticoid. In this embodiment of the combination of the present invention, the glucocorticoid may preferably be selected from the group consisting of dexamethasone, fluocinolone acetonide and prednisone, and it is most preferably dexamethasone.

In one further preferred combination of the present invention comprising a compound of formula I or a pharmaceutically acceptable salt thereof, a proteasome inhibitor and optionally a glucocorticoid, said combination may further comprise one or more additional pharmaceutically active agents. Particularly suitable pharmaceutically active agents are anti-tumor agents having a different mode of action to the compound of formula I or a pharmaceutically acceptable salt thereof, the proteasome inhibitor and the glucocorticoid, e.g. alkylating agents such as nitrosureas, ethylenimines, alkylsulfonates, hydrazines and triazines, and platinum based agents; plant alkaloids, taxanes, vinca alkaloids; anti-tumor antibiotics such as chromomycins, anthracyclines, and miscellaneous antibiotics such as Mitomycin and Bleomycin; anti-metabolites such as folic acid antagonists, pyrimidine antagonists, purine antagonists and adenosine deaminase inhibitors; topoisomerase inhibitors such as topoisomerase I inhibitors, topoisomerase II inhibitors, miscellaneous anti-neoplastics such as ribonucleotide reductase inhibitors, adrenocortical steroid inhibitor, anti-microtubule agents, and retinoids; protein kinases; heat shock proteins, poly-ADP (adenosine diphosphate)-ribose polymerase (PARP), hypoxia-inducible factors(HIF), proteasome, Wnt/Hedgehog/Notch signaling proteins, TNF-alpha, matrix metalloproteinase, farnesyl transferase, apoptosis pathway, histone deacetylases (HDAC), histone acetyltransferases (HAT), and methyltransferase; hormonal therapies, vascular disrupting agent, gene therapy, RNAi cancer therapy, chemoprotective agents, antibody conjugate, cancer immunotherapy such as Interleukin-2, cancer vaccines or monoclonal antibodies; and preferably DNA damaging agents, antimetabolites, topoisomerase inhibitors, anti-microtubule agents, EGFR inhibitors, HER2 inhibitors, VEGFR2 inhibitors, BRAF inhibitors, Bcr-Abl inhibitors, PDGFR inhibitors, ALK inhibitors, PLK inhibitors, MET inhibitors, epigenetic agents, HSP90 inhibitors, PARP inhibitors, CHK inhibitors, aromatase inhibitor, estrogen receptor antagonist, and antibodies targeting VEGF, HER2, EGFR, CD50, CD20, CD30, CD33, etc.

In one preferred embodiment of the combination of the present invention, the proteasome inhibitor, the compound of formula I or a pharmaceutically acceptable salt thereof and, if present, the glucocorticoid are adapted for administration concurrently, sequentially or separately. Preferably, the proteasome inhibitor, the compound of formula I or a pharmaceutically acceptable salt thereof and, if present, the glucocorticoid are adapted for administration concurrently.

In one preferred embodiment of the combination of the present invention, the proteasome inhibitor is selected from bortezomib, carfilzomib and LU-102 and the compound of formula I or a pharmaceutically acceptable salt thereof is

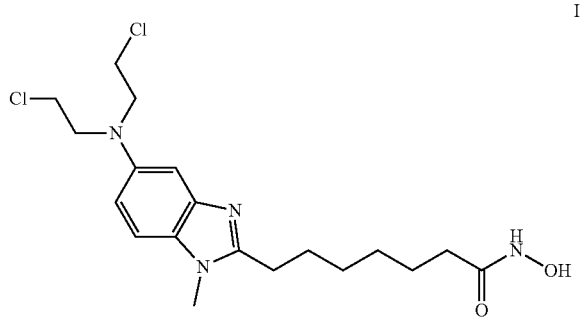 [SMILES: Cn1c(CCCCCCC(=O)NO)nc2cc(N(CCCl)CCCl)ccc21]

I or the acetate salt thereof. In one embodiment of this combination, the combination may further comprise a glucocorticoid wherein said glucocorticoid is dexamethasone.

In one preferred embodiment of the combination of the the present invention, the molar ratio of proteasome inhibitor to compound of formula I or a pharmaceutically acceptable salt thereof in said combination is from 1:1000 to 1000:1. Preferably, the molar ratio of proteasome inhibitor to compound of formula I or a pharmaceutically acceptable salt thereof in said combination is from 1:1000 to 10:1, more preferably from 1:800 to 1:200 or from 1:5 to 1:0.5, and most preferably it is from 1:700 to 1:400 or from 1:3 to 1:0.5, e.g. 1:1000, 1:900, 1:800, 1:700, 1:600, 1:500, 1:400, 1:10, 1:5, 1:4, 1:3, 1:2, 1:1 or 1:0.5.

One particularly preferred combination of present invention comprises the compound of formula I or the acetate salt thereof and a proteasome inhibitor selected from bortezomib and carfilzomib, wherein the molar ratio of the proteasome inhibitor selected from bortezomib and carfilzomib to the compound of formula I or a pharmaceutically acceptable salt thereof in said combination is from 1:700 to 1:400, e.g. 1:700, 1:600, 1:500 or 1:400. Another particularly preferred combination of the first aspect of the present invention comprises the compound of formula I or the acetate salt thereof and a proteasome inhibitor selected from LU-102, wherein the molar ratio of LU-102 to the compound of formula I or a pharmaceutically acceptable salt thereof in said combination is from 1:3 to 1:0.5, e.g. 1:3, 1:2, 1:1 or 1:0.5.

It has been surprisingly found that combinations comprising a proteasome inhibitor and a compound of formula I or a pharmaceutically acceptable salt thereof are synergistic combinations. In other words, the potency of the combinations was measured with the Calcusyn software (biosoft, Ferguson, Mo., USA), which is based on the Chou Talay method (Chou et al., *Adv. Enzyme Regul.*, 22, 27-55 (1984)), that calculates a combination index (CI) with the following interpretation:

CI 1>1: antagonist effect, CI=1: additive effect and CI<1 synergistic effect.

It was found in the present work that for many of the dual combinations of the invention comprising a proteasome inhibitor and a compound of formula I or a pharmaceutically acceptable salt, CI has been found to be less than 1, indicating synergy.

Another preferred embodiment of the combination of the present invention further comprises a glucocorticoid in addition to the proteasome inhibitor and the compound of formula I or a pharmaceutically acceptable salt thereof, wherein the molar ratio of proteasome inhibitor to the compound of formula I or a pharmaceutically acceptable salt thereof to the glucocorticoid in said combination is from 1:1000:20 to 1000:1:20. Preferably, the molar ratio of proteasome inhibitor to the compound of formula I or a pharmaceutically acceptable salt thereof to the glucocorticoid in said combination is from 1:1000:10 to 1:100:2. Preferably, the molar ratio of proteasome inhibitor to the compound of formula I or a pharmaceutically acceptable salt thereof to the glucocorticoid used in said combination is from 1:1000:5 to 1:200:2, more preferably 1:700:4 to 1:400:3, e.g. 1:1000:5, 1:900:5, 1:800:4, 1:700:4, 1:600:4, 1:500:4 or 1:400:3.

One particularly preferred combination of the the present invention comprises a proteasome inhibitor selected from bortezomib and carfilzomib, a compound of formula I or the acetate salt thereof and dexamethasone, wherein the molar ratio of the proteasome inhibitor selected from bortezomib and carfilzomib to the compound of formula I or the acetate salt thereof to dexamethasone in said combination is from 1:700:4 to 1:400:3, e.g. 1:700:4, 1:700:3, 1:600:4, 1:600:3, 1:500:3 or 1:400:3. Another particularly preferred combination of the first aspect of the present invention comprises a proteasome inhibitor selected from LU-102, the compound of formula I or the acetate salt thereof and dexamethasone, wherein the molar ratio of LU-102 to the compound of formula I or the acetate salt thereof to dexamethasone in said combination is from 1:3:4 to 1:0.5:3, e.g. 1:3:4, 1:3:3, 1:2:4, 1:2:3, 1:1:4, 1:1:3 or 1:0.5:3.

It has also been surprisingly discovered that many of the triple combinations of the present invention comprising a proteasome inhibitor, a compound of formula I or a pharmaceutically acceptable salt thereof and a glucocorticoid are also synergistic combinations, i.e. the combination index CI has been found to be less than 1.

The pharmaceutical composition according to the second aspect of the present invention comprises a pharmaceutically acceptable diluent or carrier and a combination according to the first aspect of the present invention. Preferred compositions of the second invention include those comprising the preferred combinations of the present invention as described and exemplified above. The pharmaceutically acceptable diluent or carrier of the pharmaceutical composition according to the second aspect of the present can be any suitable dispersant, excipient, adjuvant, or other material which acts as a carrier for the active agents of the combination of the present invention and which does not interfere with the active agents present in said combination. Examples of typical pharmaceutically acceptable carriers and diluents may be found in "Remington's Pharmaceutical Sciences" by E. W. Martin and these include water, saline, dextrose solution, serum solution, Ringer's solution, polyethylene glycol (e.g PEG400), a surfactant (e.g Cremophor), a cyclopolysaccharide (e.g hydroxypropyl-β-cyclodextrin or sulfobutyl ether β-cyclodextrins), a polymer, a liposome, a micelle, a nanosphere, etc.

In the third aspect of the present invention, there is provided a kit comprising a combination according to the first aspect of the present invention and, optionally, instructions for treating a patient. Typically, a kit can comprise a compound of formula I or pharmaceutically acceptable salt thereof, a proteasome inhibitor, and a glucocorticoid together with instructions for treating a patient. Each active agent can be provided in a suitable container. The kit may further comprise a delivery system, e.g. for the compound of formula I or pharmaceutically acceptable salt thereof, the proteasome inhibitor or the glucocorticoid or any combination thereof.

The instructions may advise administering the proteasome inhibitor, the compound of formula I or a pharmaceutically acceptable salt thereof and, if present, the glucocorticoid of the combination concurrently, sequentially or separately according to variables such as the specific condition being treated, the state of that condition, the activity of the specific compounds employed; the specific combination employed; the age, body weight, general health, sex and diet of the patient; the time of administration, route of administration, and rate of excretion of the specific compounds employed; the duration of the treatment; drugs used in combination or contemporaneously with the specific compounds employed; and like factors well known in the medical arts. Preferred kits according to the third aspect of the present invention include those comprising the preferred combinations of the present invention as described and exemplified above.

In the fourth aspect of the present invention, there is provided the combination, composition or kit according to the first, second or third aspect of the present invention for use in the treatment of cancer.

In the fifth aspect of the present invention, there is provided a method of treating cancer in a patient in need thereof comprising administering to said patient the combination, composition or kit according to the first, second or third aspect of the present invention.

It has been found that the combinations, compositions and kits of the present invention are highly active both in vitro and in vivo against a wide variety of tumour cell types. The anti-tumour activity shown by these double and triple combinations of the present invention, and by the combinations in the compositions and kits of the present invention is, in many cases, more than merely additive, showing combination indexes CI of significantly less than 1, indicating synergy for these combinations. This surprising finding is a further support for the particular effectiveness of the combinations, compositions and kits of the present invention in the treatment of cancer.

Examples of cancers which are treatable by the combinations, compositions and kits of the present invention include hematologic cancers such as multiple myeloma, lymphoma and leukemia, breast cancer, lung cancer, colorectal cancer, prostate cancer, testicular cancer, pancreatic cancer, liver cancer, stomach cancer, biliary tract cancer, esophageal cancer, gastrointestinal stromal tumor, cervical cancer, ovarian cancer, uterine cancer, renal cancer, melanoma, basal cell carcinoma, squamous cell carcinoma, bladder cancer, sarcoma, mesothelioma, thymoma, myelodysplastic syndrome, glioblastoma and myeloproliferative disease. In particular, the combinations, compositions and kits of the present invention are effective against hematologic cancer such as multiple myeloma, lymphoma and leukemia, and breast cancer.

In one embodiment of the combination, composition or kit for use in the treatment of a cancer according to the fourth aspect of the present invention or the method of treatment in accordance with the fifth aspect of the present invention, the cancer is selected from a hematologic cancer and breast cancer.

Where the combination, composition or kit of the present invention is for use in the treatment of a hematologic cancer, this may preferably be selected from multiple myeloma (e.g. active myeloma, plasmacytoma, light chain myeloma or non-secretory myeloma, with all forms being treatable in all phases including relapsed and refractory phases), lymphoma (e.g. Hodgkin lymphoma or non-Hodgkin lymphoma) and leukemia [acute lymphoblastic leukemia (ALL), chronic lymphocytic leukemia (CLL), acute myeloid leukemia (AML, including myeloblastic leukemia, acute promyelocytic leukemia, acute myelomonocytic leukemia, acute monocytic leukemia, acute erythroleukemia and acute megakaryotic leukemia, with all forms being treatable in all phases including relapsed and refractory phases), chronic myeloid leukemia (CML), hairy cell leukemia (HCL), T-cell prolymphocytic leukemia (T-PLL), large granular lymphocytic leukemia or T-cell acute lymphoblastic leukemia].

Where the combination, composition or kit of the present invention is for use in the treatment of breast cancer, the breast cancer may typically be selected from claudin-low tumors, basal-like tumors, human epidermal growth factor receptor 2 (HER2) positive tumors, luminal A tumors and luminal B tumors, and it is preferably a triple-negative breast cancer.

In one preferred embodiment of the combination, composition or kit for use in the treatment of cancer according to the present invention and the method of treatment of cancer according to the present invention, the proteasome inhibitor, the compound of formula I or a pharmaceutically acceptable salt thereof and, if present, the glucocorticoid are administered concurrently, sequentially or separately. More preferably, the proteasome inhibitor, the compound of formula I or a pharmaceutically acceptable salt thereof and, if present, the glucocorticoid are administered concurrently.

In the combination for use in the treatment of cancer and the method of treatment of cancer in accordance with the present invention, the compound of formula I or a pharmaceutically acceptable salt thereof is typically administered to the patient in need thereof at a dosage range of 10 to 100 mg/kg body weight patient, and preferably at a dosage range of 40 to 80 mg/kg body weight patient. Typically, the proteasome inhibitor is administered to the patient in need thereof at a dosage range of 0.01 to 0.3 mg/kg body weight patient, more preferably at a dosage range of 0.05 to 0.15 mg/kg body weight patient. Where a glucocorticoid is also administered in the combination, the glucocorticoid is typically administered at a dosage range of from 0.1 to 1 mg/kg body weight patient. Preferably, it is administered at a dosage range of from 0.3 to 0.5 mg/kg body weight patient.

The therapeutically effective amount of a combination, composition or kit according to the present invention is an amount of the combination, composition or kit which confers a therapeutic effect in accordance with the fourth and fifth aspects of the present invention on the treated subject, at a reasonable benefit/risk ratio applicable to any medical treatment. The therapeutic effect may be objective (i.e. measurable by some test or marker) or subjective (i.e. subject gives an indication of or feels an effect). An effective amount of the combination, composition or kit according to the present invention is believed to be one wherein the compound of formula I or a salt thereof is included in the combination at a dosage range of from 10 to 100 mg/kg body weight patient (e.g. 40 to 80 mg/kg body weight such as 40, 50, 60, 70 or 80 mg/kg body weight), the proteasome inhibitor is included at a dosage range of from 0.01 to 0.3 mg/kg body weight patient (e.g. 0.1 to 1 mg/kg such as 0.1, 0.2, 0.3, 0.4 or 0.5 mg/kg body weight) and the glucocorticoid is included at a dosage range of from 0.03 to 1 mg/kg body weight patient (e.g. 0.3 to 0.5 mg/kg body weight patient, such as 0.3, 0.4 or 0.5 mg/kg body weight patient).

Effective doses will vary depending on route of administration, as well as the possibility of co-usage with other active agents. It will be understood, however, that the total daily usage of the combinations, compositions and kits of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The present invention is also directed to the use of a combination, composition or kit according to the first, second or third aspect of the present invention in the manufacture of a medicament for the treatment of cancer, e.g. for the treatment of a hematologic cancer or breast cancer.

Suitable examples of the administration form of the combination, composition or kit of the present invention include without limitation oral, topical, parenteral, sublingual, rectal, vaginal, ocular, and intranasal. Parenteral administration includes subcutaneous injections, intravenous, intramuscular, intrasternal injection or infusion techniques. Preferably, the combinations, compositions and kits are administered parenterally. Combinations and compositions of the invention can be formulated so as to allow a combination or composition of the present invention to be bioavailable upon administration of the combination or composition to an animal, preferably human. Compositions can take the form of one or more dosage units, where for example, a tablet can be a single dosage unit, and a container of a combination or composition of the present invention in aerosol form can hold a plurality of dosage units.

Preferably the combinations of the present invention are provided in the form of kits. Typically, a kit includes a proteasome inhibitor, a compound of formula I or a pharmaceutically acceptable salt thereof and, optionally, a glucocorticoid. In certain embodiments, a kit can include one or more delivery systems, e.g. the proteasome inhibitor, the compound of formula I or a pharmaceutically acceptable salt thereof and, optionally, a glucocorticoid, or any combination thereof, and directions for the use of the kit (e.g. instructions for treating a subject). These directions/instructions may advise administering the proteasome inhibitor, the compound of formula I or a pharmaceutically acceptable salt thereof and, if present, the glucocorticoid of the combination concurrently, sequentially or separately according to variables such as the specific condition being treated, the state of that condition, the activity of the specific compounds employed; the specific combination employed; the age, body weight, general health, sex and diet of the patient; the time of administration, route of administration, and rate of excretion of the specific compounds employed; the duration of the treatment; drugs used in combination or contemporaneously with the specific compounds employed; and like factors well known in the medical arts.

The pharmaceutically acceptable diluent or carrier can be particulate, so that the compositions are, for example, in tablet or powder form. The carrier(s) can be liquid, with the combinations, compositions or kits being, for example, an oral syrup or injectable liquid. In addition, the carrier(s) can be gaseous, so as to provide an aerosol composition useful in, for example, inhalatory administration. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the combination, composition or kit of the present invention and the pharmaceutically acceptable carriers are sterile. Water is a preferred carrier when the combination or composition of the present invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

When intended for oral administration, the combination, composition or kit may be in solid or liquid form, where semi-solid, semi-liquid, suspension and gel forms are included within the forms considered herein as either solid or liquid.

As a solid composition for oral administration, the combination, composition or kit can be formulated into a powder, granule, compressed tablet, pill, capsule, chewing gum, wafer or the like form. Such a solid composition typically contains one or more inert diluents, either as a single tablet comprising all active agents or as a number of separate solid compositions, each comprising a single active agent of the combination of the present invention (in the case of the kit). In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

When the combination or composition is in the form of a capsule (e. g. a gelatin capsule), it can contain, in addition to materials of the above type, a liquid carrier such as polyethylene glycol, cyclodextrin or a fatty oil.

The combination, composition or kit can be in the form of a liquid, e. g. an elixir, syrup, solution, emulsion or suspension. The liquid can be useful for oral administration or for delivery by injection. When intended for oral administration, a combination, composition or kit can comprise one or more of a sweetening agent, preservatives, dye/colorant and flavor enhancer. In a combination or composition for administration by injection, one or more of a surfactant, preservative, wetting agent, dispersing agent, suspending agent, buffer, stabilizer and isotonic agent can also be included. In the kit of the present invention, the liquid components comprising one or more of the active agents of the composition may either be combined prior to administration and administered concurrently or each active agent may be administered sequentially or separately.

The preferred route of administration is parenteral administration including, but not limited to, intradermal, intramuscular, intraperitoneal, intravenous, subcutaneous, intranasal, epidural, intranasal, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, the present combinations, compositions and kits of the present invention are administered intravenously.

The liquid combinations, compositions and kits of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral combination or composition can be enclosed in an ampoule, a disposable syringe or a multiple-dose vial made of glass, plastic or other material. Physiological saline is a preferred adjuvant.

For administration (e.g. intravenous) the combination, composition or kit may typically comprise the compound of formula I or a salt thereof at a dosage range of from 10 to 100 mg/kg body weight patient, the proteasome inhibitor at a dosage range of from 0.01 to 0.3 mg/kg body weight patient and the glucocorticoid at a dosage range of from 0.03 to 1 mg/kg body weight patient. More preferably, the combination, composition or kit may typically comprise the compound of formula I or a salt thereof at a dosage range of from 40 to 80 mg/kg body weight patient, the proteasome inhibitor ata dosage range of from 0.05 to 0.15 mg/kg body weight patient and the glucocorticoid at a dosage range of from 0.3 to 0.5 mg/kg body weight patient.

The combinations of the inventions may be formulated such that the proteasome inhibitor, the compound of formula I or a pharmaceutically acceptable salt thereof and, if present, the optional glucocorticoid of the combination are adapted for administration concurrently, sequentially or separately. Preferably, they are administered concurrently.

The combination, composition or kit of the present invention can be administered by any convenient route, for example by infusion or bolus injection, by absorption through epithelial or mucocutaneous linings.

In specific embodiments, it can be desirable to administer one or more combinations, compositions or kits of the present invention or combinations, compositions or kits locally to the area in need of treatment. In one embodiment, administration can be by direct injection at the site (or former site) of a cancer, tumor or neoplastic or pre-neoplastic tissue.

Pulmonary administration can also be employed, e. g. by use of an inhaler or nebulizer, and formulation with an aerosolizing agent, or via perfusion in a fluorocarbon or synthetic pulmonary surfactant. In certain embodiments, the combination, composition or kit of the present invention or compositions can be formulated as a suppository, with traditional binders and carriers such as triglycerides.

The present combination, composition or kit can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

The pharmaceutical combinations, compositions and kits can be prepared using methodology well known in the pharmaceutical art. For example, a composition intended to be administered by injection can be prepared by combining the components of a kit of the present invention with water so as to form a solution. A surfactant can be added to facilitate the formation of a homogeneous solution or suspension.

The combinations, compositions and kits of the present invention are particularly effective in the treatment of cancer.

The combinations of the present invention have been shown to have excellent activity against a wide variety of tumor cell types both in vitro and in vivo, making them particularly interesting for development for use in the treatment of cancer, e.g. hematologic cancer and breast cancer.

It has also discovered in the present work that the compound of formula I or a salt thereof can be administered in combination with radiotherapy in the treatment of glioblastoma. Both in vitro and in vivo studies showed that a combination of the compound of formula I or a salt thereof together with radiotherapy was far more effective than radiotherapy alone. There is a prior disclosure in WO 2013/113838 of data for the compound of formula I tested in the CNS Cancer (Glioma) cell lines SF-268, SF-295, SF-539, SNB-19, SNB-75 and U-251. These suggest activity for the compound of formula I against glioblastoma when used on its own.

EXAMPLES

In the following examples, the compound having the following formula I is referred to as EDO-S101 (or EDO in the Figures):

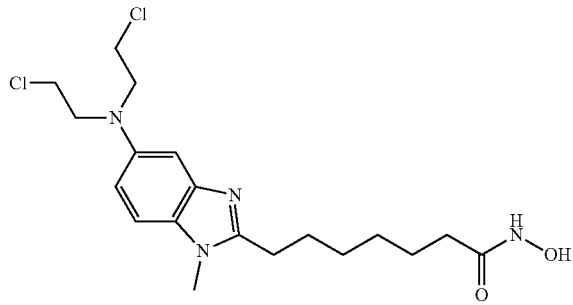

I

Example 1

EDO-S101 Combinations In Vitro—Multiple Myeloma MM1S Cell Line

EDO-S101 was combined in vitro with bortezomib and dexamethasone in the multiple myeloma MM1S cell line kindly provided by Steven Rosen at Northwestern University, Chicago, Ill., USA. Activity was measured by the MTT assay that is based on the metabolic bromide reduction from 3-(4,5-dimethylthiazol-2-yl)-2,5-diphenyltetrazole (MTT), which is produced by the mitochondrial enzyme succinatedehydrogenase, turned to a blue-colored compound named formazan. The mitochondrial functionality of the treated cells is then determined. This method has been extensively used to measure cell proliferation and survival capacities. The remaining living cells are proportional to the amount of formazan produced.

In brief the methodology was as follows:

- 30,000 MM1S cells per well were plated into the 96-well microtiter plates.
- EDO-S101 and PI dilutions were prepared in DMSO and dexamethasone in ethanol and added into the wells to the final concentrations indicated in the experiment.
- Plates were incubated for 24-48-72 hours in the incubator at 37° C. in a humidified atmosphere in the presence of 5% $CO_2$/95% air.
- After the incubation 10 µL of MTT solution were added in each well and incubated for 2 hours to allow formazan crystal formation.
- 100 µl of a mix solution with SDS plus HCl (10 µL of HCl for each 12 mL of SDS) was added to dissolve the formazan crystals.
- Absorbance was read at 570 nm OD and use a reference wavelength of 650 nm.
- Cell viability (percentage) was obtained as follows: % Viability=OD treated cells×100/OD control cells.
- Each dose was tested in quadruplicate and each experiment was performed at least twice.

The concentrations for the different drugs were ratio constant for all the experiments. EDO-S101 at 500 nM, 1 µM, 2.5 µM; dexamethasone at 2.5 nM; 5 nM; 10 nM; and bortezomib at 0.75 nM, 1.5 nM, 3 nM.

The results are as shown in Table 1 below and FIG. 1.

TABLE 1

| 48 H | | | |
|---|---|---|---|
| CI For experimental values | | | |
| Dexa 48 (nM) | EDO 48 h (nM) | Fa | CI |
| 2.5 | 500 | 0.43453 | 0.851 |
| 5 | 1000 | 0.56838 | 0.761 |
| 10 | 2000 | 0.683802 | 0.765 |
| CI For experimental values | | | |
| Bortz 48 h (nM) | EDO 48 h (nM) | Fa | CI |
| 0.75 | 500 | 0.247333 | 1.087 |
| 1.5 | 1000 | 0.452958 | 1.230 |
| 3 | 2000 | 0.918526 | 0.627 |
| CI For experimental values | | | |
| Dexa 48 h (nM) | DOBLE Bortz 48 h (nM) | Fa | CI |
| 2.5 | 0.75 | 0.413191 | 1.105 |
| 5 | 1.5 | 0.620757 | 0.879 |
| 10 | 3 | 0.935984 | 0.494 |
| CI For experimental values | | | |
| Dexa 48 h (nM) | Bortz 48 h (nM) | EDO 48 h (nM) | Fa | CI |
| 2.5 | 0.75 | 150 | 0.455868 | 0.958 |
| 5 | 1.5 | 300 | 0.673133 | 0.789 |
| 10 | 3 | 600 | 0.962173 | 0.404 |

The potency of the combination was quantitated with the Calcusyn software (biosoft, Ferguson, Mo., USA), which is based on the Chou Talay method (Chou et al., *Adv. Enzyme Regul.*, 22, 27-55 (1984)), that calculates a combination index (CI) with the following interpretation:

CI 1>1: antagonist effect, CI=1: additive effect and CI<1 synergistic effect.

It can be seen from the FIG. 1 and from above that EDO-S101 shows synergy with both bortezomib and also shows synergy in a triple combination with bortezomib and dexamethasone.

In a further experiment, the same constant dose of these drugs was incubated for 72 hours instead of 48 hours. The results are as shown in Table 2 below and FIG. 2

TABLE 2

| 72 H | | | |
|---|---|---|---|
| CI For experimental values | | | |
| DEXA (nM) | EDO (nM) | Fa | CI |
| 2.5 | 500 | 0.576413 | 0.682 |
| 5 | 1000 | 0.69365 | 0.836 |
| 10 | 2000 | 0.828332 | 0.829 |

TABLE 2-continued

| 72 H | | | |
|---|---|---|---|
| CI For experimental values | | | |
| BORTZ (nM) | EDO (nM) | Fa | CI |
| 0.75 | 500 | 0.310537 | 1.336 |
| 1.5 | 1000 | 0.780181 | 1.166 |
| 3 | 2000 | 0.999302 | 0.489 |

| CI For experimental values | | | |
|---|---|---|---|
| DEXA (nM) | BORTZ (nM) | Fa | CI |
| 2.5 | 0.75 | 0.411026 | 1.441 |
| 5 | 1.5 | 0.865318 | 0.876 |
| 10 | 3 | 1 | 0.017 |

| CI For experimental values | | | | |
|---|---|---|---|---|
| DEXA (nM) | BORTZ (nM) | EDO (nM) | Fa | CI |
| 2.5 | 0.75 | 500 | 0.607118 | 1.115 |
| 5 | 1.5 | 1000 | 0.923936 | 0.845 |
| 10 | 3 | 2000 | 1 | 0.017 |

Figure 2:
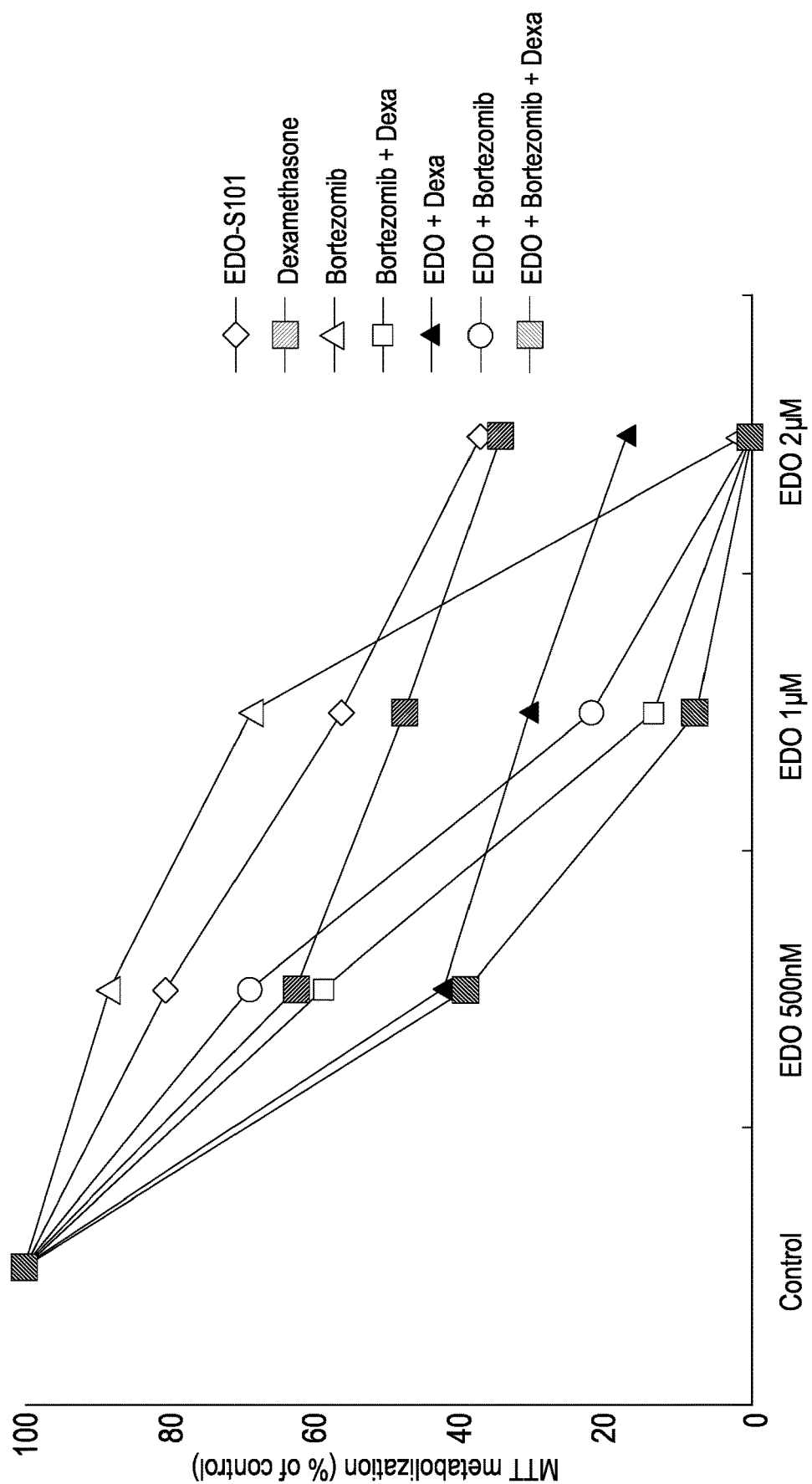
FIG. 2 is a plot of the % surviving in vitro MM1S multiple myeloma cells as a % of control versus concentration for different tested compounds after 72 hours incubation, for single compounds and as combinations (double and triple)

Again, it can be seen from FIG. 2 and the above results in Table 2 that EDO-S101 shows synergy with bortezomib and also shows synergy in a triple combination with bortezomib and dexamethasone.

Example 2

EDO-S101 Combinations In Vivo Against a Xenograft of Subcutaneous Plasmacytoma

CB17-SCID mice (obtained from The Jackson Laboratory, Bar Harbor, Me.) were subcutaneously inoculated into the right flank with $3 \times 10^6$ multiple myeloma MM1S cells kindly provided by Steven Rosen at Northwestern University, Chicago, Ill., USA in 100 μL RPMI 1640 medium and 100 μL of Matrigel (BD Biosciences). When tumours became palpable, mice were randomized to 8 groups of treatment with 5 mice in each one.

The groups were:
Control (group treated with vehicle alone)
Bortezomib 1 mg/kg twice weekly intraperitoneal for three weeks
Dexamethasone 0.5 mg twice weekly intravenously for three weeks
EDO-S101 intravenously at doses of 30 mg/kg once weekly for 3 doses,
Bortezomib plus dexamethasone
Bortezomib plus EDO-S101
EDO-S101 plus dexamethasone
Triple combination of EDO-S101 plus Bortezomib and dexamethasone Caliper measurements of the tumor diameters were performed every day, and the tumor volume was estimated as the volume of an ellipse using the following formula: $V = 4/3\pi \times (a/2) \times (b/2)2$, where "a" and "b" correspond to the longest and shortest diameter, respectively.

Figure 3:
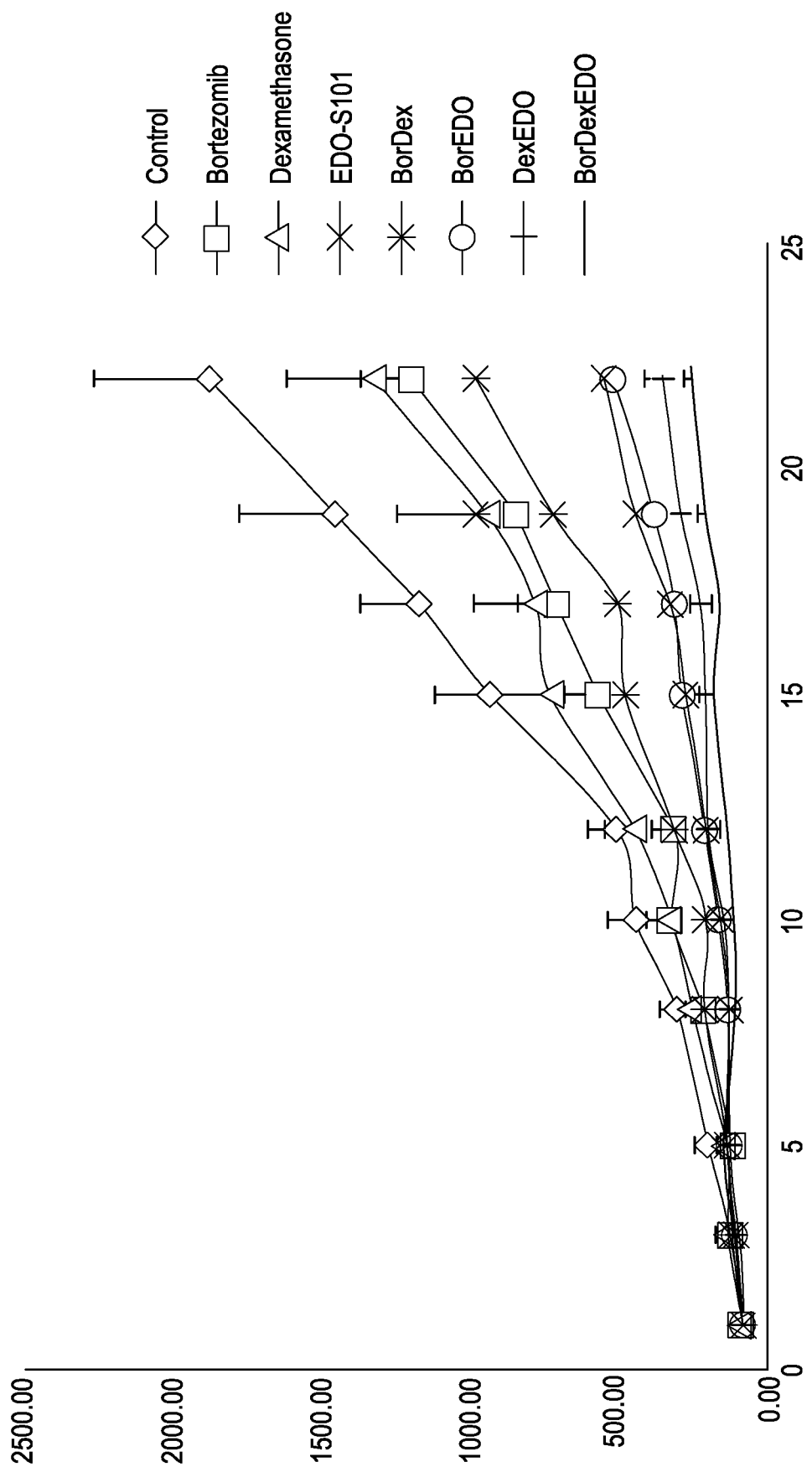
FIG. 3 is a plot of tumour growth (mm$^3$) against the number of days of study for different tested compounds for CB17-SCID mice subcutaneously inoculated into the right flank with 3×10$^6$ MM1S cells, for single compounds and as combinations.

The tumour growth results are as shown in FIG. 3 in a plot of tumour growth (mm³) against the number of days of study. It can be seen that the combination of EDO-S101 and bortezomib results in tumour volumes lower than that seen with either agent alone while the triple combination of EDO-S101, bortezomib and dexamethasone shows very significantly lower tumour volumes by the end of the study than any of the active agents individually.

Example 3

EDO-S101 Combinations In Vitro—Multiple Myeloma RPMI 8226 Cell Line

Using the same test procedure as described in Example 1, but using the multiple myeloma RPMI 8226 cell line (obtained from DMSZ) in place of the MM1S cell line, combinations of EDO-S101 with bortezomib, carfilzomib and LU-102 were tested for activity in turn. The concentrations for the different drugs were ratio constant for all the experiments. EDO-S101 at a concentration of 0, 2, 4, 8 μM; each of bortezomib and carfilzomib at a concentration of 0, 5, 10, 20 nM; and LU-102 at a concentration of 0, 1, 3.3, 10 μM. Controls with bendamustin were also performed.

Figure 4:
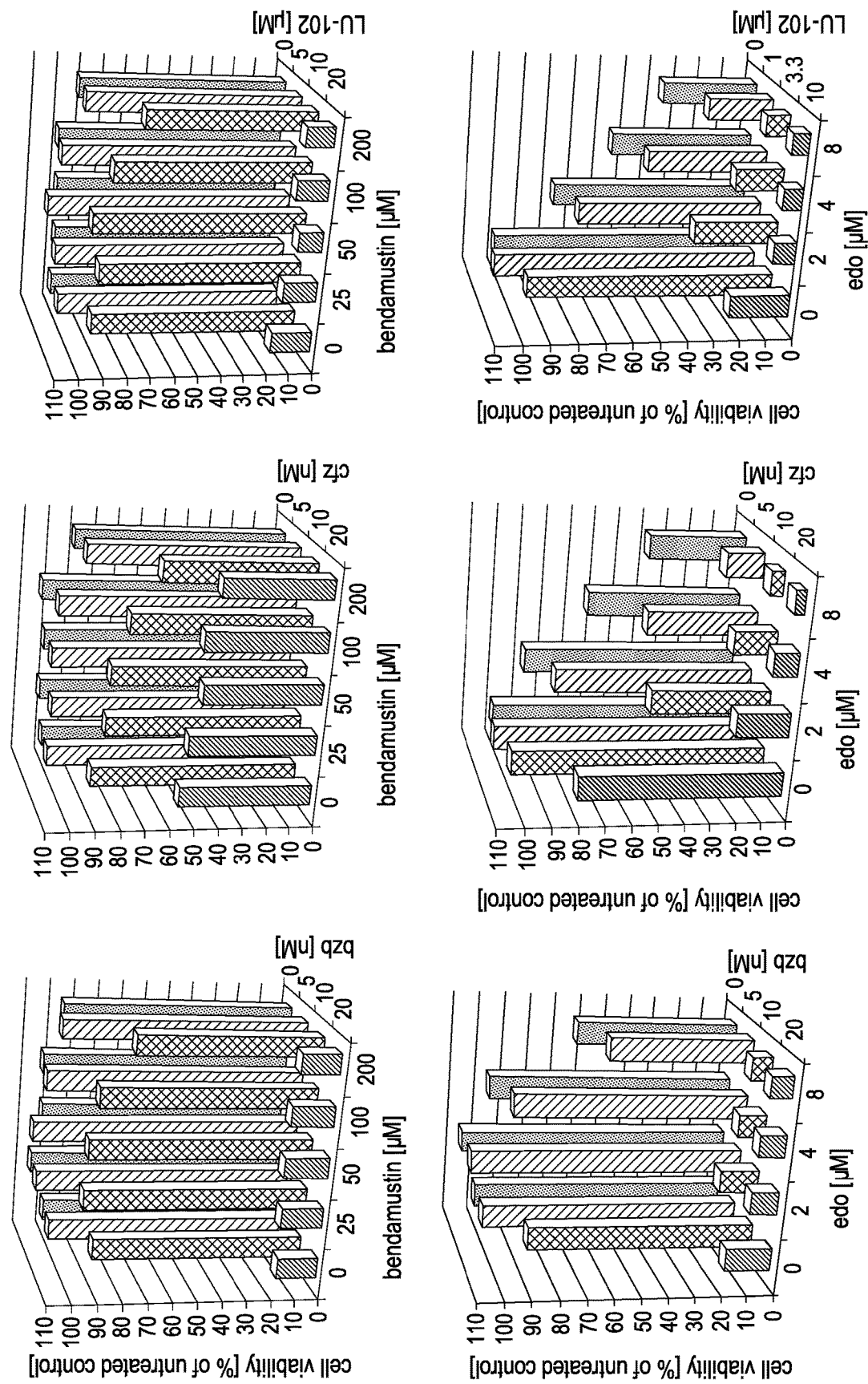
FIG. 4 is a plot of the % surviving in vitro RPMI8226 multiple myeloma cells as a % of control versus concentration for different tested compounds after 48 hours incubation, for single compounds and as combinations (double)

The cell viability as a percentage of the untreated control was measured and the results are as shown in FIG. 4. The figure shows clear synergy for each of the three combinations with EDO-S101 in vitro against multiple myeloma RPMI 8226. The CI at 4 μM EDO-S101 and 20 nm carfilzomib was 0.019 and the CI at 4 μM EDO-S101 and 3 μM LU-102 was 0.109.

Example 4

EDO-S101 Combinations In Vitro—Multiple Myeloma Cell Line 2013-10-16 MTS AMO abzb Using the same test procedure as described in Example 1, but using the bortezomib resistant multiple myeloma 2013-10-16 MTS AMO abzb cell line (generated at the Department of Oncology and Hematology of the Kantonsspital St. Gallen by Prof. Dr. med. C. Driessen) in place of the MM1S cell line, combinations of EDO-S101 with bortezomib, carfilzomib and LU-102 were tested for activity in turn. The concentrations for the different drugs were ratio constant and were 0, 2, 4, 8 μM for EDO-S101; 0, 1.25, 2.5, 5, 10, 20 nM for each of bortezomib and carfilzomib; and 0, 1, 3.3, 10 for LU-102.

Figure 5:
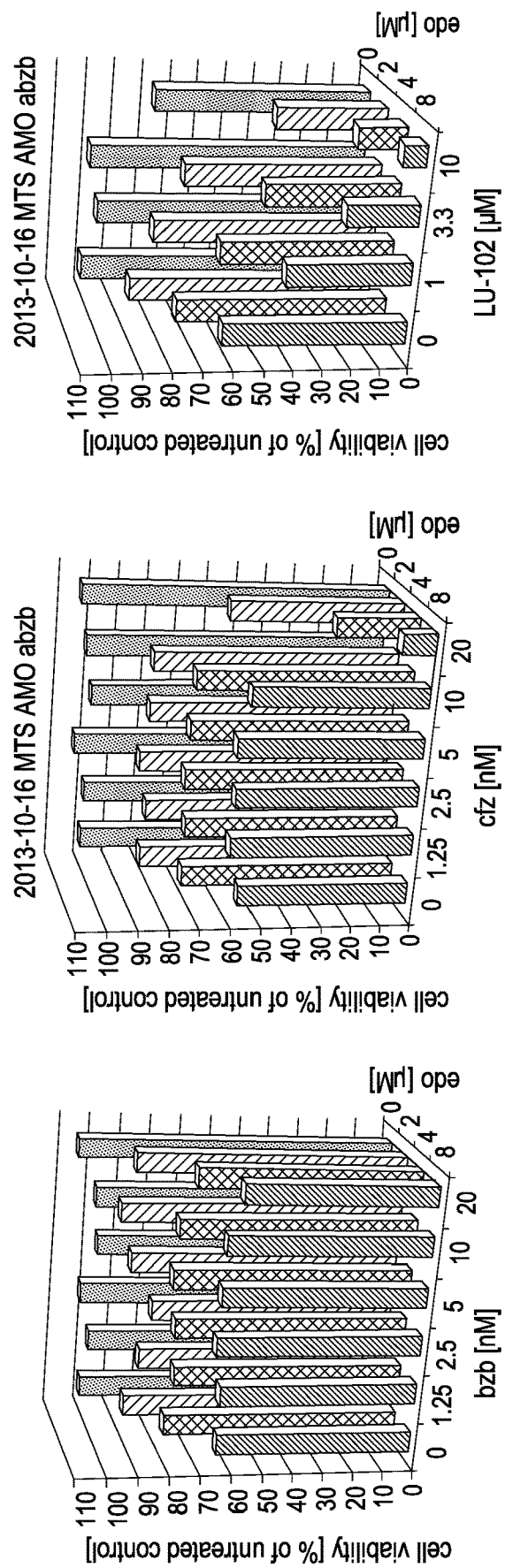
FIG. 5 is a plot of the % surviving in vitro 2013-10-16 MTS AMO abzb multiple myeloma cells as a % of control versus concentration for different tested compounds after 48 hours incubation, for single compounds and as combinations (double)

The cell viability as a percentage of the untreated control was measured and the results are as shown in FIG. 5. The figure shows clear synergy for the combinations of carfilzomib and LU-102 with EDO-S101 in vitro against the bortezomib resistant multiple myeloma 2013-10-16 MTS AMO abzb. The CI for the combinations of EDO-S101 and carfilzomib against this cell line was 0.11 and that for EDO-S101 and LU-102 was 0.25.

Example 5

EDO-S101 Combinations In Vitro—Mantle Cell Lymphoma Cell Line 2014-01-15 MTS Jeko Using the same test procedure as described in Example 1, ut using the mantle cell lymphoma cell line 2014-01-15 MTS Jeko (obtained from LGC Standards S.a.r.l., 6, rue Alfred Kastler, BP 83076, F-67123 Molsheim Cedex, France) in place of the MM1S cell line, combinations of EDO-S101 with bortezomib, carfilzomib and LU-102 were tested for activity in turn. The concentrations for the different drugs were ratio constant for all the experiments and the same as in Example 3.

Figure 6:
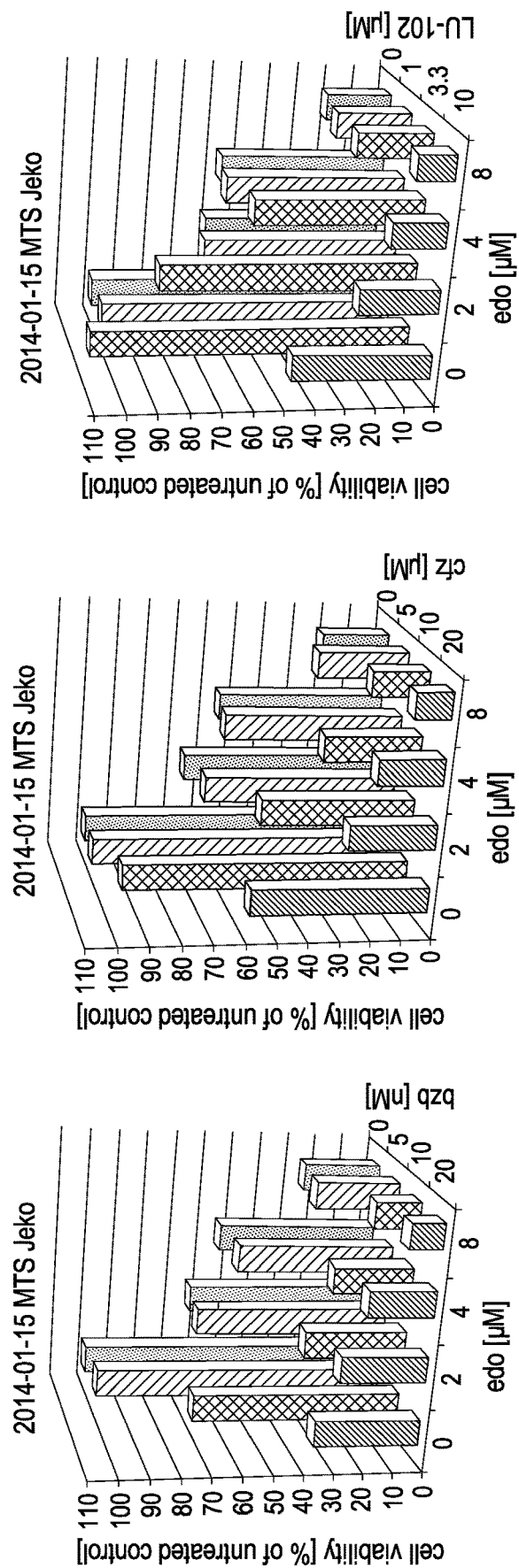
FIG. 6 is a plot of the % surviving in vitro 2014-01-15 MTS Jeko mantle cell lymphoma cells as a % of control versus concentration for different tested compounds after 48 hours incubation, for single compounds and as combinations (double)

The cell viability as a percentage of the untreated control was measured and the results are as shown in FIG. 6. The figure shows clear synergy for each of the three combinations with EDO-S101 in vitro against mantle cell lymphoma cell line 2014-01-15 MTS Jeko. The CI at 2 µM EDO-S101 and 20 nm bortezomib was 0.292; the CI at 2 µM EDO-S101 and 20 nm carfilzomib was 0.206; and the CI at 2 µM EDO-S101 and 10 µM LU-102 was 0.204.

Example 6

EDO-S101 Combinations In Vitro—Mantle Cell Lymphoma Cell Line 2014-01-15 MTS Granta Using the same test procedure as described in Example 1, but using the mantle cell lymphoma cell line 2014-01-15 MTS Granta (obtained from LGC Standards S.a.r.l., 6, rue Alfred Kastler, BP 83076, F-67123 Molsheim Cedex, France) in place of the MM1S cell line, combinations of EDO-S101 with bortezomib, carfilzomib and LU-102 were tested for activity in turn. The concentrations for the different drugs were ratio constant for all the experiments and the same as in Example 3.

Figure 7:
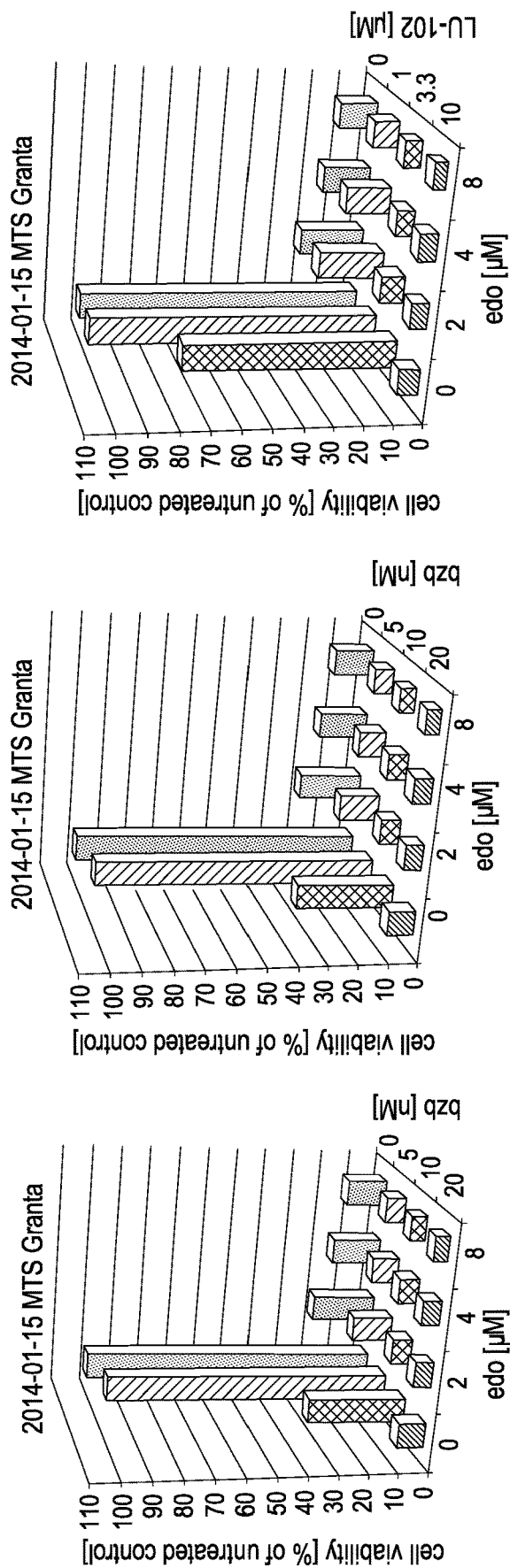
FIG. 7 is a plot of the % surviving in vitro 2014-01-15 MTS Granta mantle cell lymphoma cells as a % of control versus concentration for different tested compounds after 48 hours incubation, for single compounds and as combinations (double)

The cell viability as a percentage of the untreated control was measured and the results are as shown in FIG. 7. The figure shows clear synergy for each of the three combinations with EDO-S101 in vitro against mantle cell lymphoma cell line 2014-01-15 MTS Granta. The CI at 0.5 µM EDO-S101 and 8 nm bortezomib was 0.025; the CI at 0.5 µM EDO-S101 and 8 nm carfilzomib was 0.089; and the CI at 1 µM EDO-S101 and 3 µM LU-102 was 0.078.

Example 7

EDO-S101 Combinations In Vitro—Basal Like Breast Cancer Cell Line MTS MDA-MB468

Using the same test procedure as described in Example 1, but using the basal like breast cancer cell line MTS MDA-MB468 (obtained from LGC Standards S.a.r.l., 6, rue Alfred Kastler, BP 83076, F-67123 Molsheim Cedex, France) in place of the MM1S cell line, combinations of EDO-S101 with bortezomib, carfilzomib and LU-102 were tested for activity in turn. The concentrations for the different drugs were ratio constant for all the experiments and were 0, 2, 4, 8 and 16 µM for EDO-S101; 0, 8, 16 and 32 nM for each of bortezomib and carfilzomib; and 0, 1, 3.3 and 10 µM for LU-102.

Figure 8:
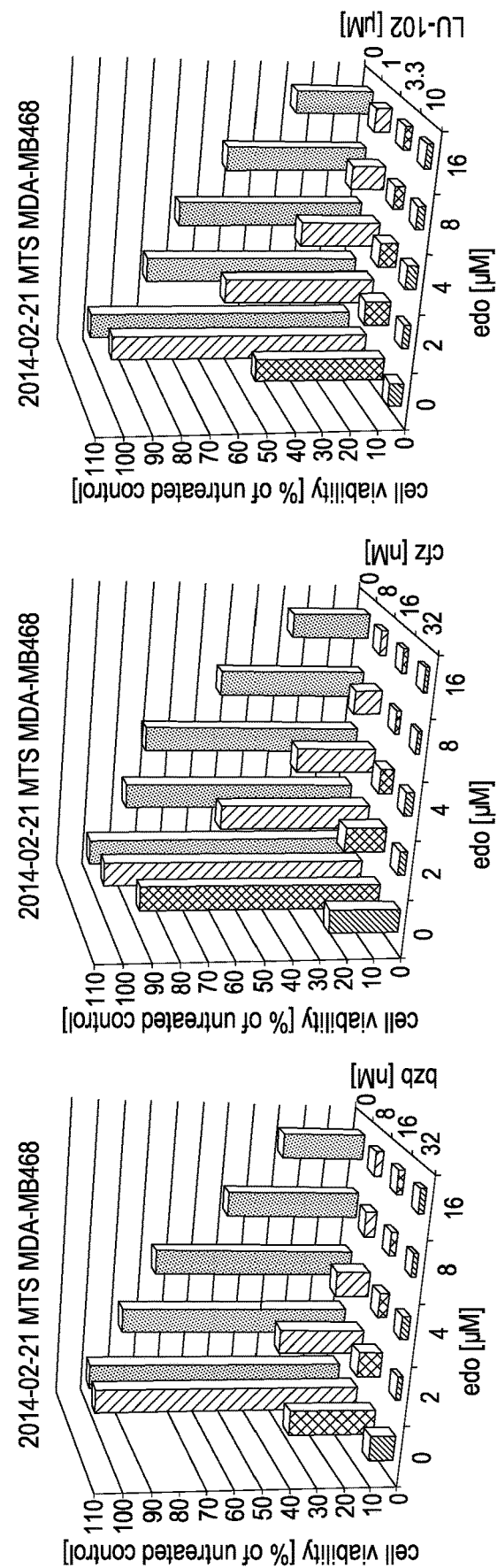
FIG. 8 is a plot of the % surviving in vitro 2014-02-21 MTS MTS MDA-MB468 basal like breast cancer cells as a % of control versus concentration for different tested compounds after 48 hours incubation, for single compounds and as combinations (double)

The cell viability as a percentage of the untreated control was measured and the results are as shown in FIG. 8. The figure shows clear synergy for each of the three combinations with EDO-S101 in vitro against this triple negative breast cancer cell line MTS MDA-MB468.

Example 8

EDO-S101 Combinations In Vitro—Promyelocytic Leukemia Cell Line HL-60

Using the same test procedure as described in Example 1, but using the promyelocytic leukemia cell line HL-60 (obtained from LGC Standards S.a.r.l., 6, rue Alfred Kastler, BP 83076, F-67123 Molsheim Cedex, France) in place of the MM1S cell line, combinations of EDO-S101 with bortezomib, carfilzomib and LU-102 were tested for activity in turn. The concentrations for the different drugs were ratio constant for all the experiments and were 0, 1, 2 and 4 µM for EDO-S101; 0, 5, 10, 20 nM for bortezomib and carfilzomib; and LU-102 for 0, 1, 3.3, 10 µM.

Figure 9:
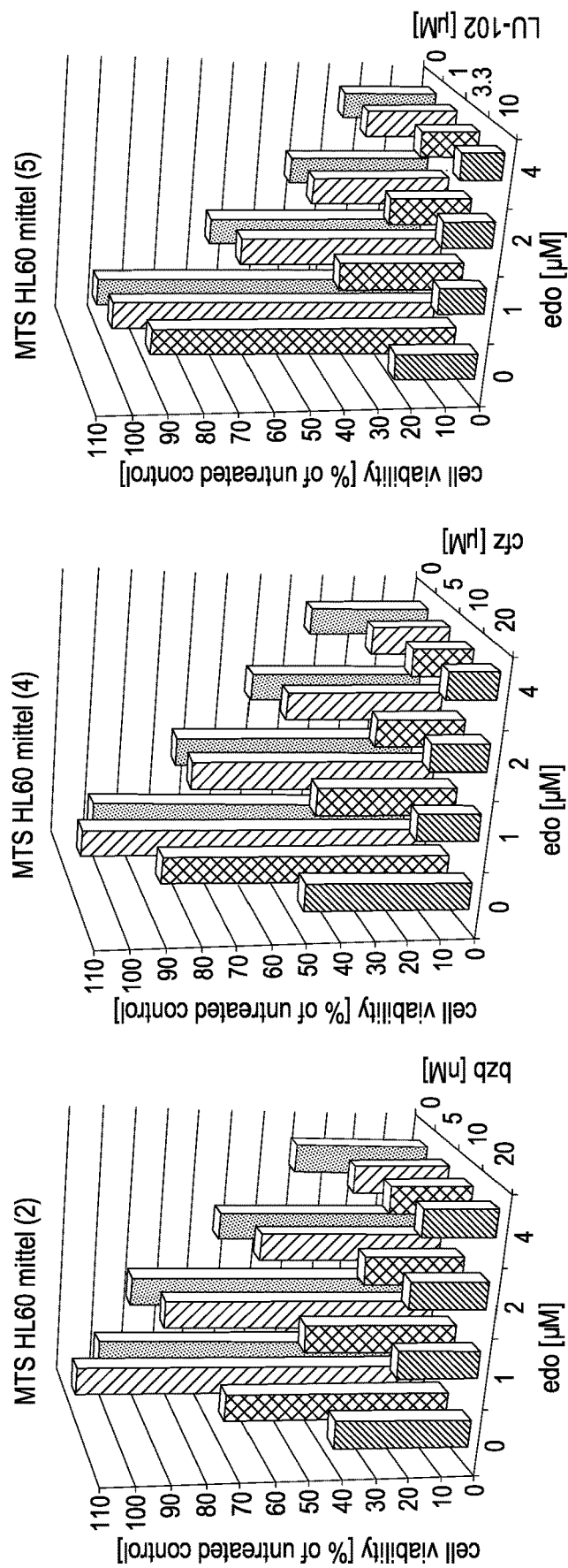
FIG. 9 is a plot of the % surviving in vitro MTS HL-60 promyelocytic leukemia cells as a % of control versus concentration for different tested compounds after 48 hours incubation, for single compounds and as combinations (double)

The cell viability as a percentage of the untreated control was measured and the results are as shown in FIG. 9. The figure shows clear synergy for each of the three combinations with EDO-S101 in vitro against promyelocytic leukemia cell line HL-60. The CI at 1 µM EDO-S101 and 20 nm bortezomibzomib was 0.051; the CI at 1 µM EDO-S101 and 20 nm carfilzomib was 0.073; and the CI at 1 µM EDO-S101 and 3 µM LU-102 was 0.387.

Example 9

EDO-S101 Combinations In Vitro—Acute Myeloid Leukemia Cell Line U937

Using the same test procedure as described in Example 1, but using the acute myeloid leukemia cell line U937 (obtained from LGC Standards S.a.r.l., 6, rue Alfred Kastler, BP 83076, F-67123 Molsheim Cedex, France) in place of the MM1S cell line, combinations of EDO-S101 with bortezomib, carfilzomib and LU-102 were tested for activity in turn. The concentrations for the different drugs were ratio constant for all the experiments and were the same as in Example 8.

Figure 10:
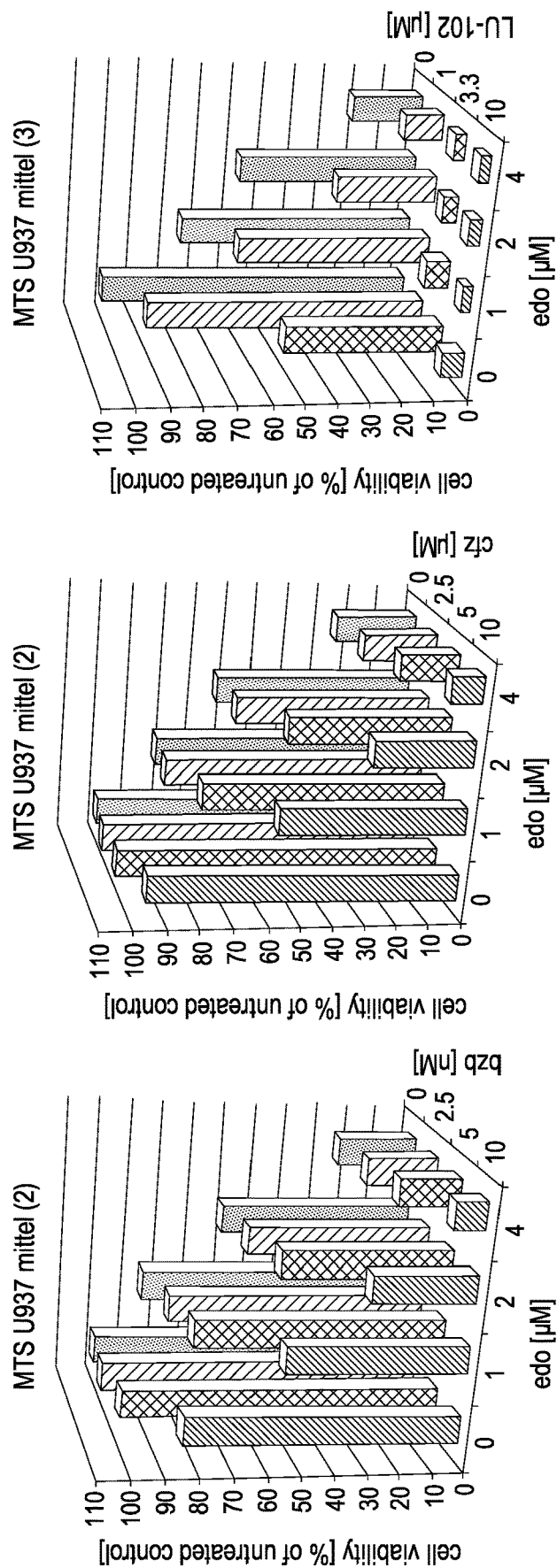
FIG. 10 is a plot of the % surviving in vitro MTS U937 acute myeloid leukemia cells as a % of control versus concentration for different tested compounds after 48 hours incubation, for single compounds and as combinations (double)

The cell viability as a percentage of the untreated control was measured and the results are as shown in FIG. 10. The figure shows clear synergy for each of the three combinations with EDO-S101 in vitro against basal like acute myeloid leukemia cell line U937. The CI at 2 µM EDO-S101 and 10 nm bortezomib was 0.285; the CI at 2 µM EDO-S101 and 10 nm carfilzomib was 0.272; and the CI at 2 µM EDO-S101 and 3 µM LU-102 was 0.095.

Example 10

EDO-S101 Combinations In Vitro—B Cell Lymphoma Cell Line BJAB

Using the same test procedure as described in Example 1, but using the B cell lymphoma cell line BJAB (germinal center line) (obtained from LGC Standards S.a.r.l., 6, rue Alfred Kastler, BP 83076, F-67123 Molsheim Cedex, France) in place of the MM1S cell line, combinations of EDO-S101 with bortezomib, carfilzomib and LU-102 were tested for activity in turn. The concentrations for the different drugs were ratio constant for all the experiments and were the same as in Example 8.

Figure 11:
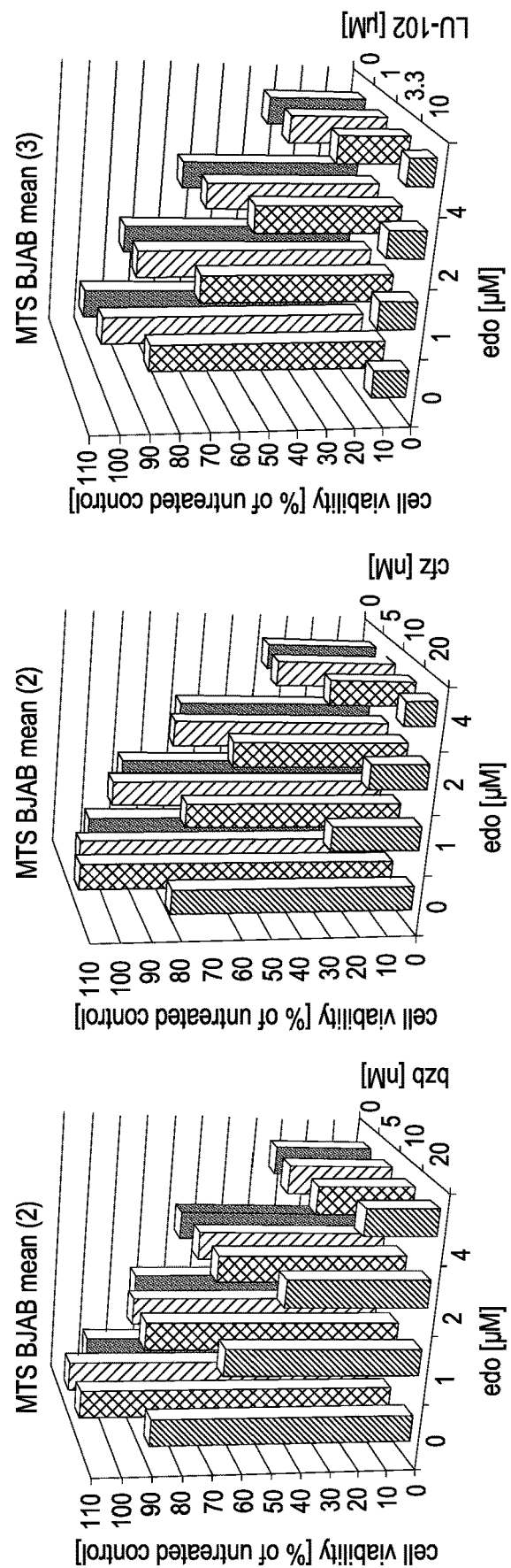
FIG. 11 is a plot of the % surviving in vitro BJAB (germinal center line) B cell lymphoma cells as a % of control versus concentration for different tested compounds after 48 hours incubation, for single compounds and as combinations (double)

The cell viability as a percentage of the untreated control was measured and the results are as shown in FIG. 11. The figure shows strong synergy for the combination of EDO-S101 and carfilzomib in particular in vitro against B cell lymphoma cell line BJAB (germinal center line), while the combination of EDO-S101 and bortezomib also showed synergy. The CI for the combination of EDO-S101 and carfilzomib was 0.09, while the CI for the combination of EDO-S101 and bortezomib was 0.62.

Example 11

EDO-S101 Combinations In Vitro—B Cell Lymphoma Cell Line OciLy3

Using the same test procedure as described in Example 1, but using the B cell lymphoma cell line OciLy3 (ABC-type) (obtained from LGC Standards S.a.r.l., 6, rue Alfred Kastler, BP 83076, F-67123 Molsheim Cedex, France) in place of the MM1S cell line, combinations of EDO-S101 with bortezomib, carfilzomib and LU-102 were tested for activity in turn. The concentrations for the different drugs were ratio constant for all the experiments and were 0, 0.5, 1 and 2 µM for EDO-S101, 0, 5, 10 and 20 nM for bortezomib and carfilzomib and 0, 1, 3.3 and 10 µM for LU-102.

Figure 12:
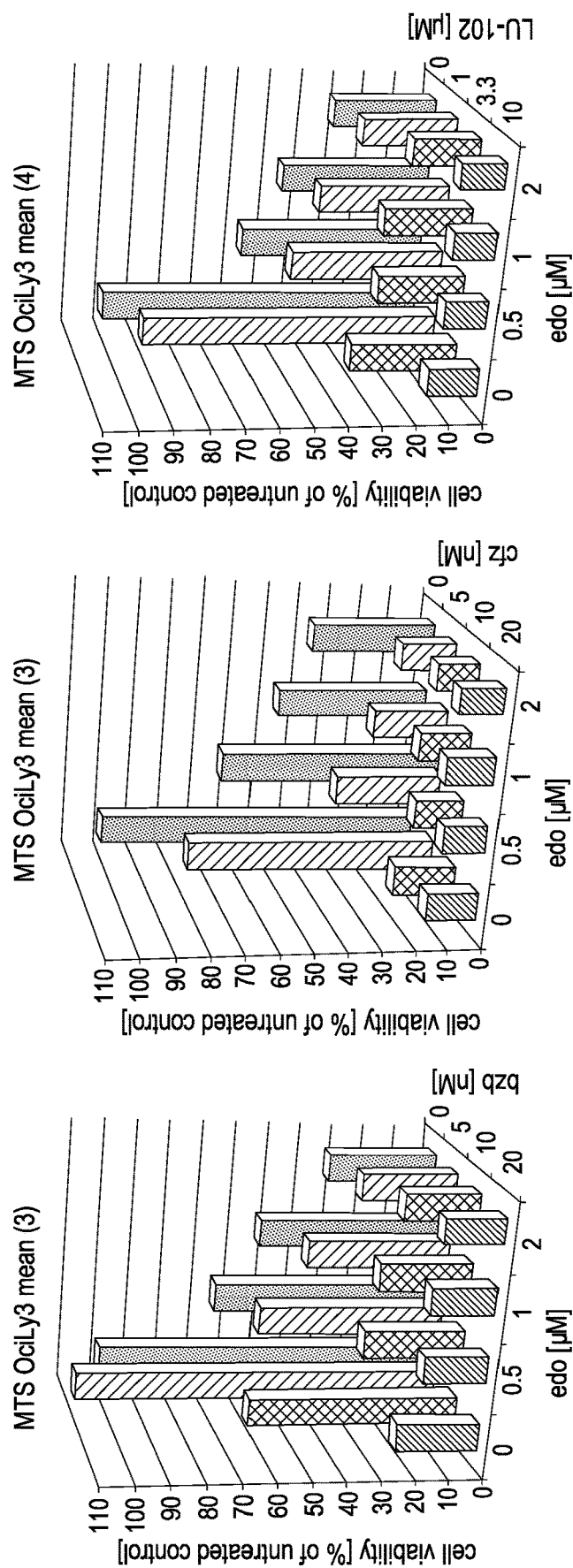
FIG. 12 is a plot of the % surviving in vitro OciLy3 (ABC-type) B cell lymphoma cells as a % of control versus concentration for different tested compounds after 48 hours incubation, for single compounds and as combinations (double)

The cell viability as a percentage of the untreated control was measured and the results are as shown in FIG. 12. The figure shows strong synergy for the combination of EDO-S101 and bortezomib in particular in vitro against B cell lymphoma cell line OciLy3 (ABC-type), while the combination of EDO-S101 and carfilzomib also showed synergy. The CI for the combination of EDO-S101 and carfilzomib was 0.59, while the CI for the combination of EDO-S101 and bortezomib was 0.21.

Example 12

EDO-S101 Combinations In Vitro—B Cell Lymphoma Cell Line TMD8

Using the same test procedure as described in Example 1, but using the B cell lymphoma cell line TMD8 (ABC-type) (obtained from LGC Standards S.a.r.l., 6, rue Alfred Kastler, BP 83076, F-67123 Molsheim Cedex, France) in place of the MM1S cell line, combinations of EDO-S101 with bortezomib, carfilzomib and LU-102 were tested for activity in turn. The concentrations for the different drugs were ratio constant for all the experiments and were the same as in Example 11.

Figure 13:
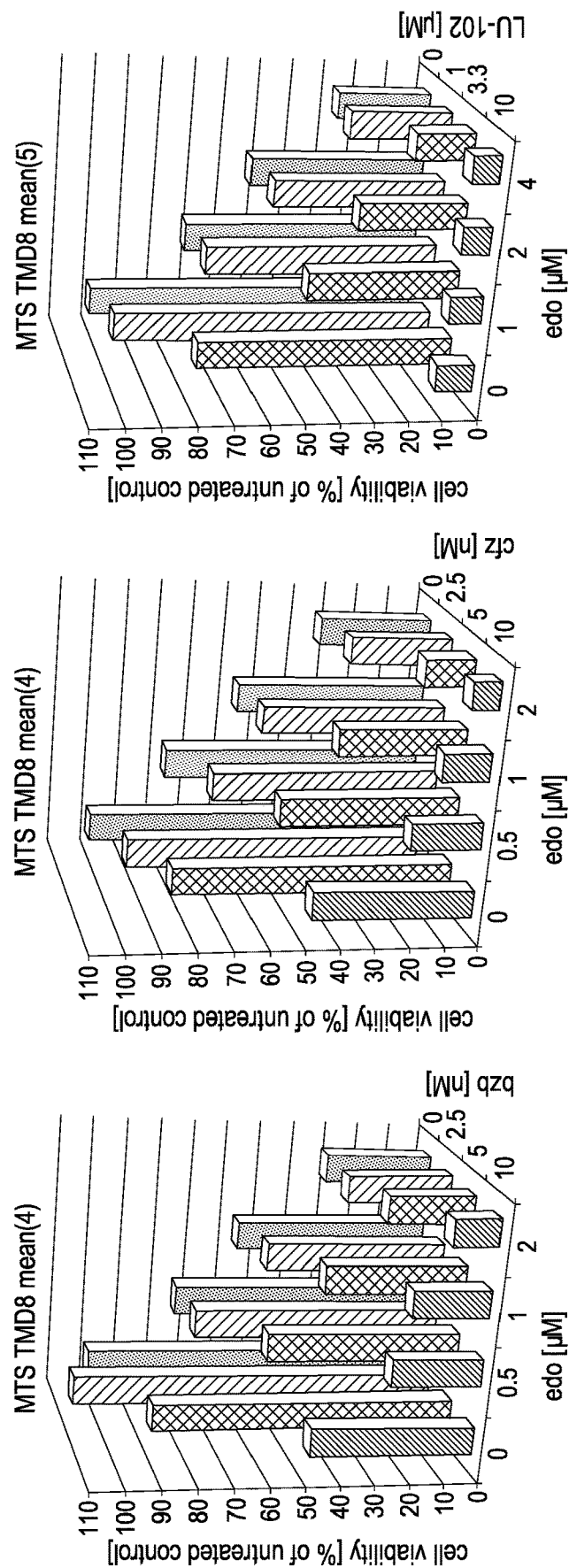
FIG. 13 is a plot of the % surviving in vitro TMD8 (ABC-type) B cell lymphoma cells as a % of control versus concentration for different tested compounds after 48 hours incubation, for single compounds and as combinations (double)

The cell viability as a percentage of the untreated control was measured and the results are as shown in FIG. 13. The figure shows strong synergy for all combinations of EDO-S101 and proteasome inhibitor tested. The CI for the combination of EDO-S101 and carfilzomib was 0.17, the CI for the combination of EDO-S101 and bortezomib was 0.14 and the CI for the combination of EDO-S101 and LU-102 was 0.63.

Example 13

EDO-S101 Combinations In Vitro—Triple Negative Breast Cancer Cell Line BT-549

Using the same test procedure as described in Example 1, but using the triple negative breast cancer cell line BT-549 (obtained from LGC Standards S.a.r.l., 6, rue Alfred Kastler, BP 83076, F-67123 Molsheim Cedex, France) in place of the MM1S cell line, combinations of EDO-S101 with bortezomib, carfilzomib and LU-102 were tested for activity in turn. The concentrations for the different drugs were ratio constant for all the experiments and were 0, 1, 2 and 4 µM for EDO-S101; 0, 5, 10 and 20 nM for each of bortezomib and carfilzomib; and 0, 1, 3.3 and 10 µM for LU-102.

Figure 14:
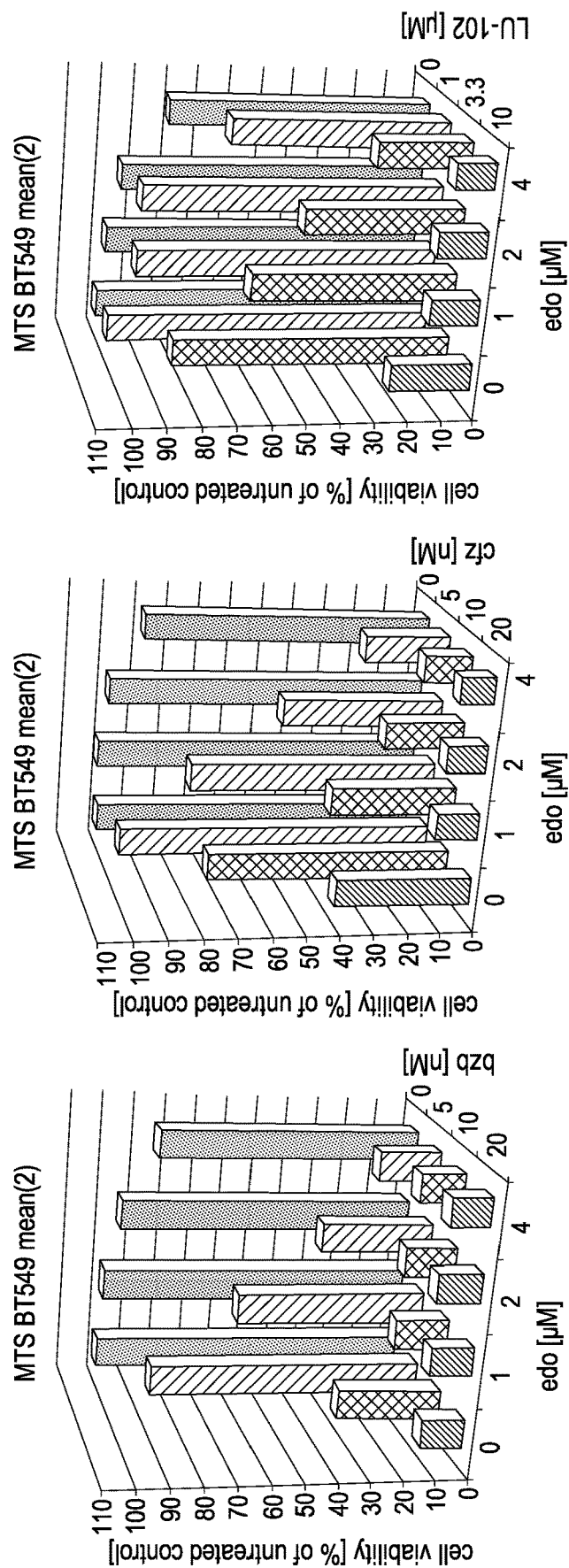
FIG. 14 is a plot of the % surviving in vitro BT-549 triple negative breast cancer cells as a % of control versus concentration for different tested compounds after 48 hours incubation, for single compounds and as combinations (double)

The cell viability as a percentage of the untreated control was measured and the results are as shown in FIG. 14. The figure shows clear synergy for each of the three combinations with EDO-S101 in vitro against triple negative breast cancer cell line BT-549. The CI for the combination of EDO-S101 and bortezomib was 0.14, the CI for the combination of EDO-S101 and carfilzomib was 0.05 and the CI for the combination of EDO-S101 and LU-102 was 0.38.

Example 14

Combinations of Radiotherapy and EDO-S101 Against Glioblastoma Cell Lines In Vitro For the U251MG glioblastoma cell line, the $IC_{50}$ was measured to be 6.60 µM for EDO-S101 (compared to 30 µM for bendamustin and 20 for temozolamide).

For the U87G glioblastoma cell line, the $IC_{50}$ was measured to be 1.36 µM for EDO-S101 (compared to 50 µM for bendamustin and 20 for temozolamide).

For the T98G glioblastoma cell line, the $IC_{50}$ was measured to be 7.70 µM for EDO-S101 (compared to 52 µM for bendamustin and >100 for temozolamide).

Figure 15:
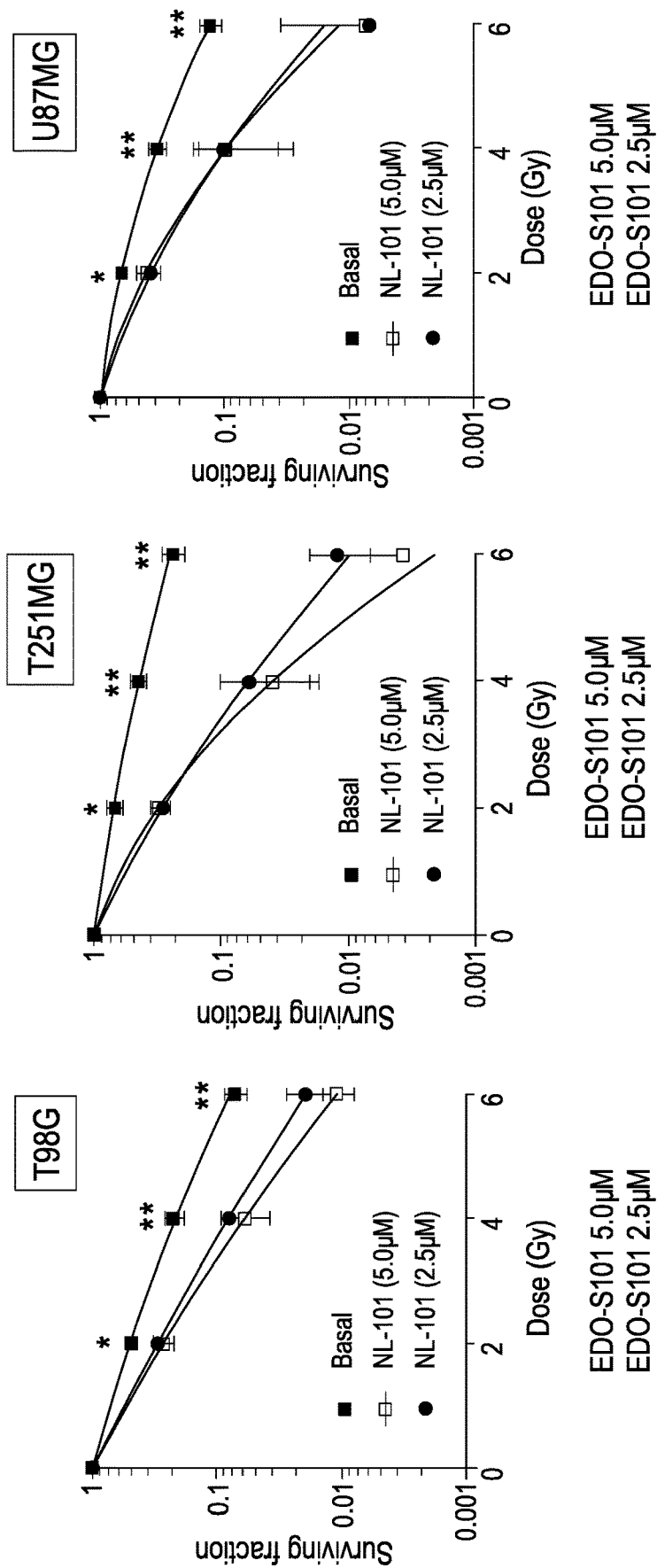
FIG. 15 is a plot of % surviving fraction of in vitro T98G, U251MG and U87MG glioblastoma cell lines against dose of radiotherapy (Gy) in combination with two different concentrations of the compound of formula I (EDO-S101) against a control with radiotherapy alone.

As can be seen from FIG. 15, the % survival rate for the glioblstoma cells was considerably reduced when radiotherapy was used in combination with a dose of EDO-S101 (5 µM or 10 µM) compared to radiotherapy alone.

Example 15

Combinations of Radiotherapy and EDO-S101 Against Glioblastoma Cell Lines In Vivo U87MG, U251MG and T98G
Subcutaneously inoculated xenografts
Treatments and Doses
Vehicle (control)
Radiotherapy (2Gy/5 consecutive days)
Temozolamide (16 mg/Kg for 5 consecutive days, po)
Temozolamide+radiotherapy
EDO-S101 (60 mg/Kg at day 1, 8 and 15 every 28 days, iv)
EDO-S101+radiotherapy It was found that the time to progression of the tumours was increased from approximately 17-18 days for the control for the U251MG mouse xenograft model, to 42 days with a combination of radiotherapy and temozolamide to over 50 days for EDO-S101 alone (significance P=0.924) to significantly over 50 days for a combination of EDO-S101 and radiotherapy (significance P=0.0359).

It was found that the time to progression of the tumours was increased from approximately 15 days for the control for the U87MG mouse xenograft model, to 35 days with a combination of radiotherapy and temozolamide to 40 days for EDO-S101 alone (significance P=2372) to significantly over 50 days for a combination of EDO-S101 and radiotherapy (significance P=0.0001).

Example 16

Activity of EDO-S101 Against Relapsed/Refractory Multiple Myeloma Models

A genetic rearrangement of the MYC locus, resulting in dysregulated expression of MYC, is the most common mutation in human multiple myeloma. The genetically engineered Vk*MYC mouse model is based on dysregulation of MYC, and has been extensively validated as a clinically and biologically faithful model of untreated multiple myeloma. Nine drugs or classes of drugs (DNA alkylators, glucocorticoids, proteasome inhibitors, IMiDs, nab-paclitaxel, histone deacetylase inhibitors, TAC1-lg, perifosine and SNS-032, a CDK2,7,9 inhibitor) have been previously reported with more than a 20% partial response rate in Vk*MYC MM. Among those, the first five also have greater than 20% PR in patients with multiple myeloma for a positive predictive value of 56%.

EDO-S101 induced a high rate of response in Vk*MYC multiple myeloma that was sustained for more than three months in mice receiving only two doses, one week apart. Remarkably EDO-S101 is the only drug that was identified with single agent activity in the very aggressive, multi-drug resistant Vk12653 transplant model of relapsed/refractory multiple myeloma.

In conclusion, it can be seen that the compound of formula I (EDO-S101) show excellent activity in combination with proteasome inhibitors in acting both in vitro and in vivo against a wide range of myeloma, lymphoma, leukemia and breast cell lines. Furthermore, it can be seen that the activity of many of these combinations is surprisingly synergistic, and in many cases to a very significant degree. Yet further, it is seen in Examples 1 and 2 that triple combinations comprising the compound of formula I, a proteasome inhibitor and a glucocorticoid such as dexamethasone showed particularly strong synergy.

As a result, it is to be expected that combinations of the compound of formula I of the present invention with a proteasome inhibitor, optionally comprising a glucocorticoid, will be of use in the treatment of cancer, particularly hematologic cancers and breast cancer.

The invention claimed is:

1. A method of treating lymphoma in a patient in need thereof, the method comprising administering to said patient a combination, said combination comprising a proteasome inhibitor and a compound of formula I or a pharmaceutically acceptable salt thereof:

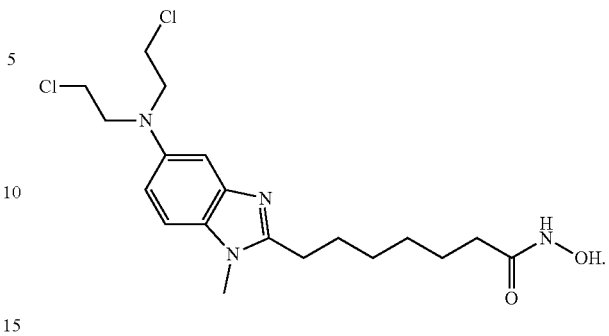

2. The method of claim 1, wherein the lymphoma is Hodgkin lymphoma.

3. The method of claim 1, wherein the lymphoma is non-Hodgkin lymphoma.

4. The method according to claim 1, wherein in said method the proteasome inhibitor, the compound of formula I or pharmaceutically acceptable salt thereof and, an optional glucocorticoid, are administered concurrently, sequentially or separately.

5. The method according to claim 1, wherein the proteasome inhibitor is administered to the patient at a dosage range of 0.01 to 0.3 mg/kg body weight patient.

6. The method according to claim 1, wherein the proteasome inhibitor is administered to the patient at a dosage range of 0.05 to 0.15 mg/kg body weight patient.

7. The method according to claim 1, wherein the combination further comprises a glucocorticoid, and wherein in the method, the glucocorticoid is administered at a dosage range of from 0.1 to 1.0 mg/kg body weight patient.

8. The method according to claim 1, wherein the combination further comprises a glucocorticoid, and wherein in the method, the glucocorticoid is administered at a dosage range of from 0.3 to 0.5 mg/kg body weight patient.

9. The method according to claim 1, wherein the lymphoma is relapsed and/or refractory.

* * * * *